US012778885B1

(12) United States Patent
Xia

(10) Patent No.: US 12,778,885 B1
(45) Date of Patent: Nov. 3, 2026

(54) METHOD FOR TRANSNASAL DELIVERY OF CANNABIDIOL AND OTHER THERAPEUTIC TREATMENTS

(71) Applicant: Tian Xia, Chicago, IL (US)

(72) Inventor: Tian Xia, Chicago, IL (US)

( * ) Notice: Subject to any disclaimer, the term of this patent is extended or adjusted under 35 U.S.C. 154(b) by 713 days.

(21) Appl. No.: 18/341,424

(22) Filed: Jun. 26, 2023

Related U.S. Application Data

(60) Provisional application No. 63/388,757, filed on Jul. 13, 2022.

(51) Int. Cl.

| | |
|---|---|
| ***A61K 9/00*** | (2006.01) |
| ***A61K 31/00*** | (2006.01) |
| ***A61K 31/403*** | (2006.01) |
| ***A61K 31/675*** | (2006.01) |
| ***A61M 11/06*** | (2006.01) |

(52) U.S. Cl.
CPC .......... *A61K 9/0073* (2013.01); *A61K 31/403* (2013.01); *A61K 31/658* (2023.05); *A61K 31/675* (2013.01); *A61M 11/06* (2013.01)

(58) Field of Classification Search
CPC .. A61K 9/0073; A61K 31/403; A61K 31/658; A61K 31/675; A61M 11/06; A61M 5/31548; A61M 5/3159–31593; A61M 15/08; A61M 5/1452; A61M 5/1456; A61M 5/14566; A61M 15/0028; A61M 2205/073; A61M 2210/0618; A61M 2202/048; A61M 19/00; A61M 11/007; A61M 11/02;
(Continued)

(56) References Cited

U.S. PATENT DOCUMENTS 6,747,058 B1 * 6/2004 Dedhiya ................ A61K 9/008
514/454
8,231,588 B2 7/2012 Xia
(Continued)

FOREIGN PATENT DOCUMENTS

WO WO 2008/120207 A2 10/2008
WO WO-2020157569 A1 * 8/2020 ......... A61K 31/4439

OTHER PUBLICATIONS

How to use Nasacort Allergy 24HR Nasal Spray accessed 20220811 (Year: 2022).*
Cuffari, "Improving the Water Solubility of CBD for Cancer Treatment," https://www.azolifesciences.com/article/Improving-the-Water-Solubility-of-CBD-for-Cancer-Treatment.aspx, Feb. 3, 202, 3 pages.
(Continued)

*Primary Examiner* — Elliot S Ruddie
(74) *Attorney, Agent, or Firm* — Crowell & Moring LLP

(57) ABSTRACT

A novel method for treating one or more of self-reported or clinically-diagnosed depression, substandard sleep quality, appetite control issues, social anxiety, general anxiety, PTSD, traumatic memory-related stress, cluster headaches, intractable phantom-limb pain (PLP), chronic pain, and/or obsessive compulsive disorders (OCD) may include transnasally delivering one or more of CBD, Dimethyltryptamine (DMT), Psilocybin, Δ8-tetrahydrocannabinol, and Δ9-tetrahydrocannabinol, or any effective variant or derivative thereof, to the sphenopalatine ganglion of a patient. This method of delivery will provide effective treatment including at least alleviating one or more symptoms of one or more of self-reported anxiety, self-reported depression, and/or self-reported substandard sleep quality, with an effective dosage amount that is administered differently than prior CBD treatments.

19 Claims, 12 Drawing Sheets

(58) Field of Classification Search
CPC ...... A61M 15/0021; A61M 2202/0241; A61M 2205/276
See application file for complete search history.

(56) References Cited

U.S. PATENT DOCUMENTS

| | | | |
|---|---|---|---|
| 8,690,839 B2 | 4/2014 | Xia et al. | |
| 8,876,794 B2 | 11/2014 | Xia | |
| 8,905,980 B2 | 12/2014 | Xia | |
| 2015/0231108 A1 | 8/2015 | Hearn et al. | |
| 2017/0312474 A1 | 11/2017 | Forde | |
| 2017/0348276 A1 | 12/2017 | Bryson et al. | |
| 2020/0170962 A1 | 6/2020 | Leweke et al. | |
| 2021/0074402 A1* | 3/2021 | Levin | G16H 20/10 |
| 2022/0032022 A1* | 2/2022 | Gold | A61M 11/006 |

OTHER PUBLICATIONS

Harvard Health Blog, "Cannabidiol (CBD)—what we know and what we don't," https://www.health.harvard.edu/blog/cannabidiol-cbd-what-we-know-and-what-we-dont-2018082414476, printed Mar. 26, 2021, 2 pages.
Kruger, et al., "Delta-8-THC: Delta-9-THC's nicer younger sibling?", Journal of Cannabis Research, (2022) 4:4, 8 pages.
Lowe, et al., "The Therapeutic Potential of Psilocybin," Molecules (2021) 26, 2948, 33 pages.
Nasadol.com, "Cannabidiol Nasal Spray, Better than CBD Oil!" Meet Israel—Dravet Syndrome video at Vimeo.com/513419764, printed Mar. 26, 2021, 13 pages.
RQS Blog, "Cannabis Nasal Sprays: Do They Really Work?", https://www.royalqueenseeds.com/blog-cannabis-nasal-sprays-do-they-really-work-n1204, printed Mar. 26, 2021, 3 pages.

* cited by examiner

FIG. 6
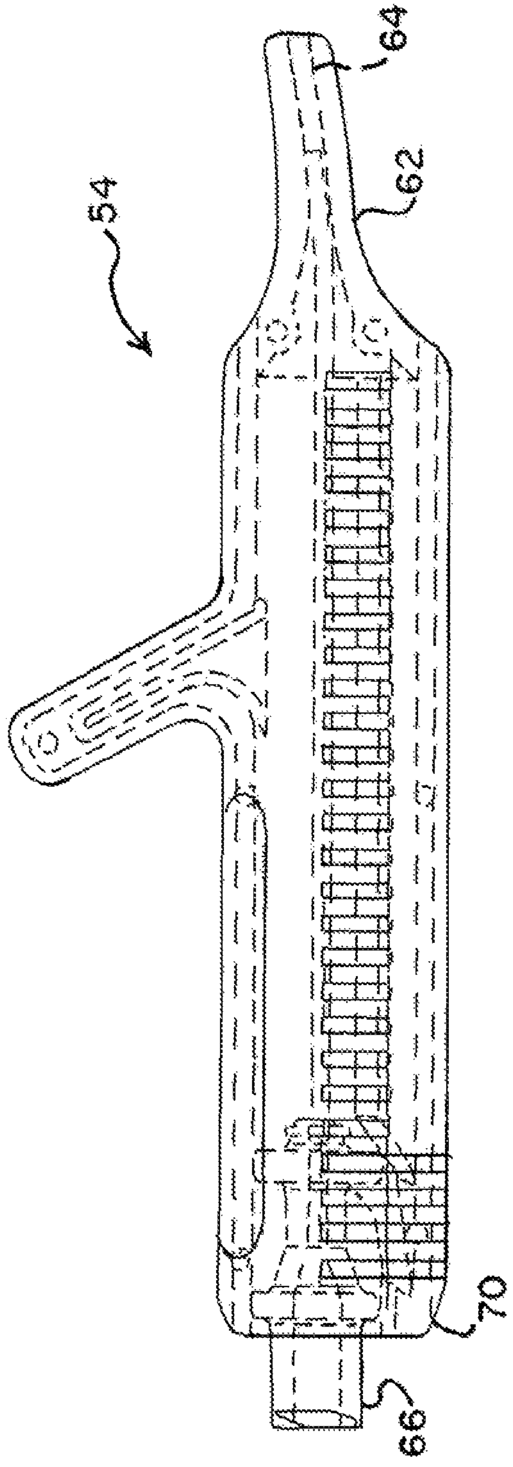
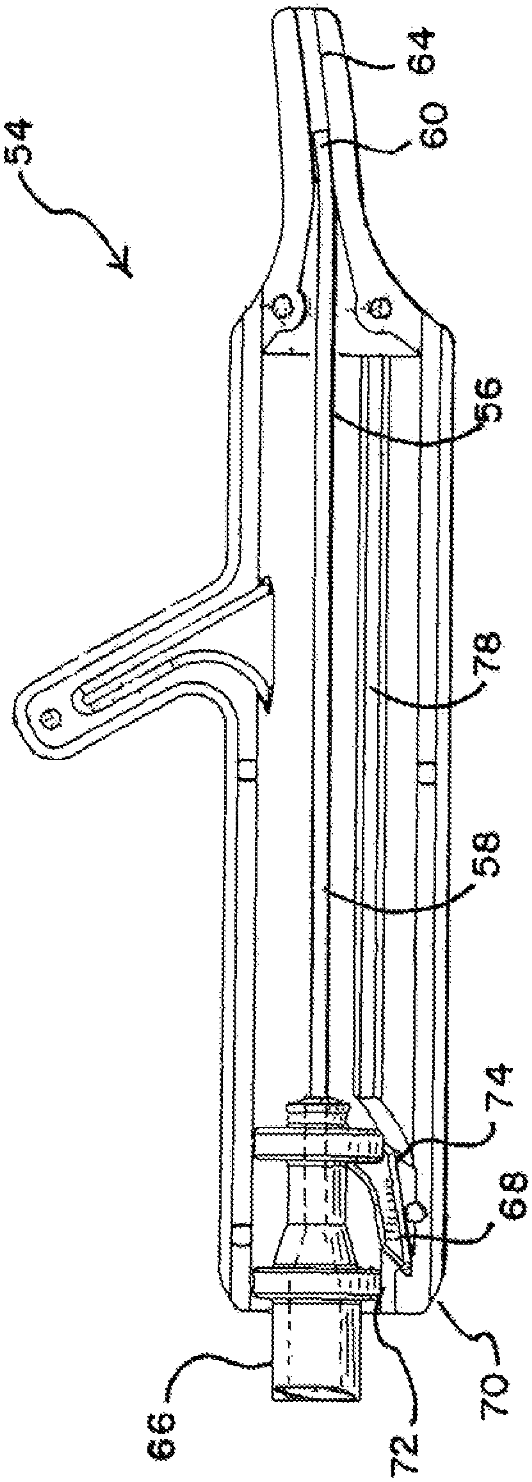
FIG. 7

METHOD FOR TRANSNASAL DELIVERY OF CANNABIDIOL AND OTHER THERAPEUTIC TREATMENTS

RELATED APPLICATIONS

The application claims the benefit of the filing date under 35 U.S.C. § 119 (e) of Provisional U.S. Patent Application Ser. No. 63/388,757, filed Jul. 13, 2022, which is hereby incorporated by reference.

TECHNICAL FIELD

Embodiments disclosed herein generally relate to a method of treatment for alleviating symptoms associated with neurological-related conditions in a mammal. More particularly, embodiments herein are directed to anatomically targeted, low-dosage delivery of cannabidiol and/or related compounds (whether derived from hemp, from *cannabis*, or synthesized), or other compounds for treatment of neurological-related conditions.

BACKGROUND

A compound of Formula I:

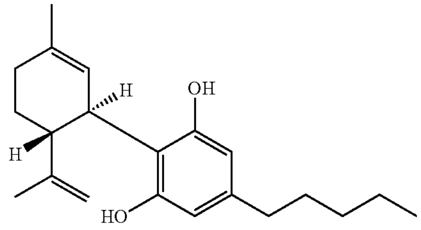 [SMILES: C=C(C)[C@@H]1CCC(C)=C[C@H]1c1c(O)cc(CCCCC)cc1O]

is designated as cannabidiol (CBD), which has gained attention and wide use for treating a variety of conditions. Unlike another hemp/cannabis-derived compound, Δ9-tetrahydracannabinol (THC) (which is regulated as a controlled substance under various state and federal laws when present above 0.3% by weight), CBD is not considered to have hallucinogenic or other effects associated with that "controlled substance" status of THC. CBD has garnered recent attention as potentially providing alleviation of a number of comfort and/or health conditions, and many forms of ingestion are currently in use including oral (consumable foods and pills), inhalable (mists, vaping, smoking/combustion), and topical (lotions, rubs, ointments, nasal sprays). See, e.g., U.S. Patent Publications US2015/0231108 A1; US2017/0312474A1; US2017/0348276A1; and US2020/0170962A1.

Topical treatments for external, transdermal use of CBD provide about 1 mg CBD to 110 mg CBD per mL of material (typically a lotion, gel, or oil in the range of 2-50 mg/mL), while commercially-available nasal sprays purport to provide about 2 mg CBD to 40 mg CBD per mL of material. See, e.g., WO 2008/120207A2.

In view of the desirability of using a minimal effective amount of CBD (including for reasons of cost and to minimize and potential undesired side effects), it may be desirable to provide a mode of delivery that is effective for treating or at least alleviating symptoms of anxiety, depression, and insomnia, different than currently-known treatment regimens. It may also be desirable to treat those conditions, as well as one or more of appetite control, social anxiety, general anxiety, PTSD, traumatic memory-related stress, cluster headaches, intractable phantom-limb pain (PLP), chronic pain, and obsessive-compulsive disorders (OCD), with one or more of CBD, Dimethyltryptamine (DMT), Psilocybin, Δ8-tetrahydrocannabinol, and Δ9-tetrahydrocannabinol.

BRIEF SUMMARY

In one aspect, embodiments disclosed herein may include methods for treating a human patient, including steps of transnasally administering to the patient a therapeutically effective amount of a medicament comprising one or more of CBD, Dimethyltryptamine (DMT), Psilocybin, Δ8-tetrahydrocannabinol, and Δ9-tetrahydrocannabinol or any effective derivative or variant thereof, wherein the transnasal administration step includes spraying from within the patient's nasal cavity in a narrowly targeted manner directed laterally and superiorly toward the sphenopalatine ganglion.

In another aspect, embodiments disclosed herein may include a method for treating or at least alleviating symptoms of a neurological or psychological disorder or other disorder in a human patient, including steps of administering a therapeutically effective amount—for treating or at least alleviating symptoms of one or more of self-reported or clinically-diagnosed depression, substandard sleep quality, appetite control issues, social anxiety, general anxiety, PTSD, traumatic memory-related stress, cluster headaches, intractable phantom-limb pain (PLP), chronic pain, and/or obsessive-compulsive disorders (OCD)—of a medicament comprising one or more of CBD, Dimethyltryptamine (DMT), Psilocybin, Δ8-tetrahydrocannabinol, and Δ9-tetrahydrocannabinol or any effective derivative or variant thereof by transnasally administering the medicament in a highly targeted manner to the sphenopalatine ganglion of a patient.

In certain embodiments a method for treating a human patient, may include steps of providing a means for delivering a medicament in a highly targeted manner to the sphenopalatine ganglion of a patient; and administering a therapeutically effective amount of a medicament for treating or at least alleviating symptoms of one or more of self-reported or clinically-diagnosed anxiety, depression, substandard sleep quality, appetite control issues, social anxiety, general anxiety, PTSD, traumatic memory-related stress, cluster headaches, intractable phantom-limb pain (PLP), chronic pain, and/or obsessive-compulsive disorders (OCD); wherein the medicament includes one or more of CBD, Dimethyltryptamine (DMT), Psilocybin, Δ8-tetrahydrocannabinol, and Δ9-tetrahydrocannabinol, or any effective derivative or variant thereof; and wherein the step of administering comprises transnasally delivering the medicament in a highly targeted manner to the sphenopalatine ganglion of the patient by directing a distal portion of the means for delivering the medicament transnasally to a location inferior and lateral of the sphenopalatine ganglion and actuating the means for delivering the medicament in a manner that directs the medicament toward the sphenopalatine ganglion in a manner that distinctively is more targeted and more effective than a nasal spray.

BRIEF DESCRIPTION OF THE DRAWINGS

FIG. 6 shows a side elevation of a second device for delivering a medicament to a patient in need thereof prior to insertion of the hub into the housing and with the injector in its storage position;

FIG. 7 shows a partial cross-sectional side view of the device of FIG. 6 with the injector in its storage position;

FIGS. 10-10D show embodiments of an introducer, where FIGS. 10A-10B and 10D are external views, FIG. 10B is a longitudinal section view taken along line 10B-10B of FIG. 10D, and FIG. 10C is a transverse section view taken along line 10C-10C of FIG. 10B;

FIGS. 10E-10G show embodiments of stop-bar-receiving channel configurations;

DETAILED DESCRIPTION

Figures 1, 2:
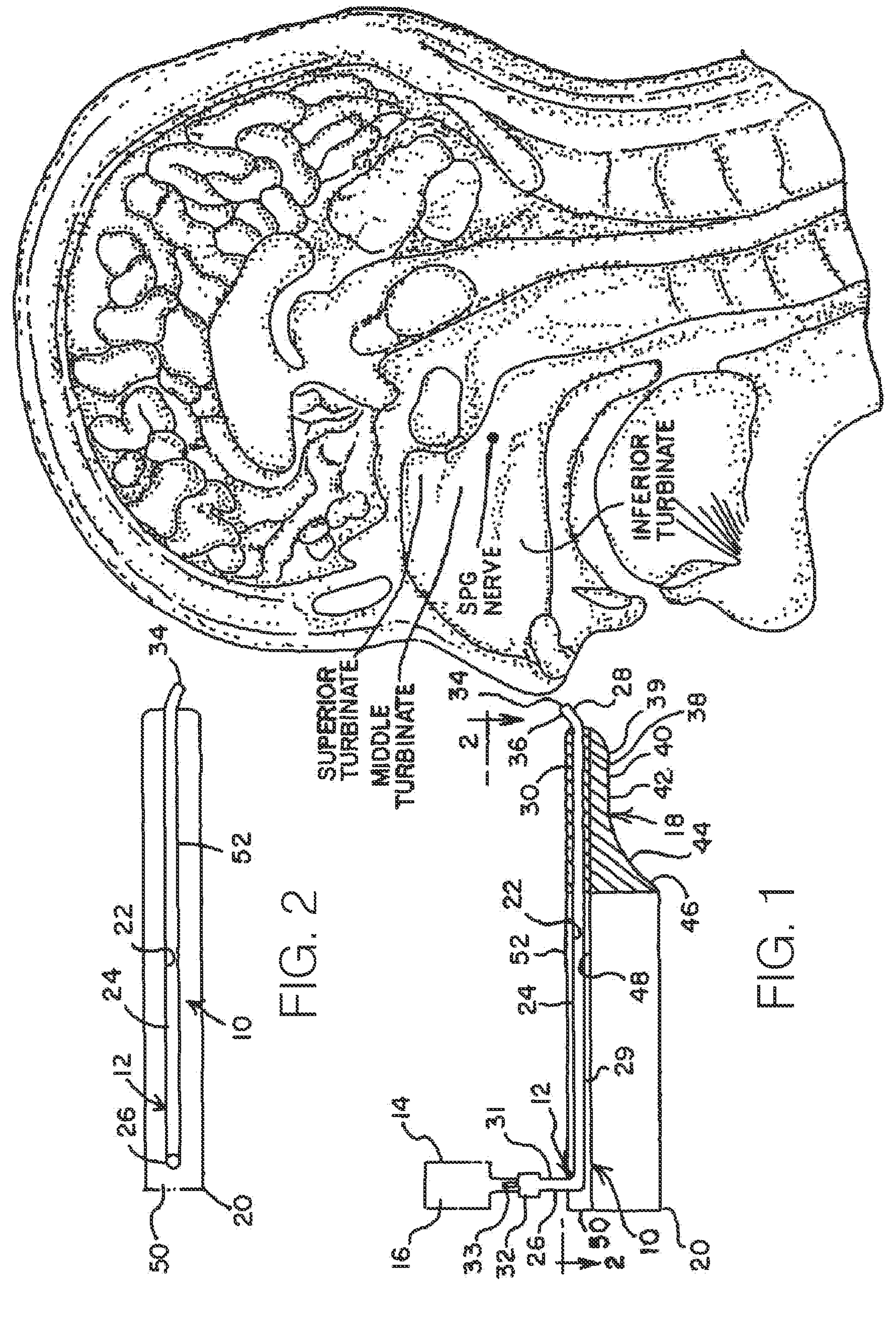
FIG. 1 shows a cross-sectional side view of a device for delivering a medicament to a patient in need thereof prior to insertion of the device into a patient's nostril in accordance with principles described herein, and showing the location of the sphenopalatine ganglion of the patient.
FIG. 2 shows a cross-sectional top plan view of the device of FIG. 1 taken along the line 2-2.

Various embodiments are described below with reference to the drawings in which like elements generally are referred to by like numerals, and those elements should be considered as exchangeable and/or able to be combined between and among all the embodiments disclosed herein. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). The terms "proximal" and "distal" are used herein in a common usage sense where they refer respectively to a handle/doctor-end of a device or related object and a tool/patient-end of a device or related object. The term "superior" refers directionally to the top of a patient's head, while "inferior" refers to the opposite direction, toward the patient's feet. The term "anteriorly" refers to the direction towards the patient's face/caudal body surface, while "posteriorly" refers to the opposite direction towards the patient's back/dorsal body surface. The term "laterally" refers to left-right relative to the patient's body. The term "about" when used with reference to any volume, dimension, proportion, or other quantitative value is intended to communicate a definite and identifiable value within the standard parameters that would be understood by one of skill in the art (equivalent to a medical device engineer with experience in the field of medicament delivery devices and/or a pharmacist experienced in methods of solution/suspension and delivery of medicaments), and should be interpreted to include at least any legal equivalents, minor but functionally-insignificant variants, and including at least mathematically significant figures and variation of +/−5% of the last significant digit. The term "therapeutically effective amount" as used herein refers to that amount of a compound being administered which will relieve to some extent one or more of the symptoms of the disorder being treated. Relief of symptoms may be quantified using one or more of patient self-reporting regarding severity of symptoms, tracking of disorder incidence frequency and/or severity (e.g., epileptic seizure, alcohol use, cocaine use, binge eating occurrence, etc.), and/or diagnostic testing means known in the medical art including at least those for evaluating patient behavior, blood chemistry, cell/tissue biopsy samples, and other standard medical diagnostic evaluation means. The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a mammal.

As used herein, the phrase "towards the sphenopalatine ganglion" (SPG) and similar such phrases used in reference to the delivery of a medicament are intended to include the SPG itself as well as the pterygopalatine fossa which houses the SPG and the sphenopalatine foramen, such that delivery of a medicament described herein shall be understood to refer to the location and/or directionality of delivery that results directly in applying the medicament to the SPG (e.g., via overlying tissue of the nasal mucosa, which overlying tissue should be understood as being included when the present disclosure references delivery to/toward the SPG). It is believed that the proximity of the SPG and surrounding tissue to the brain, including shared circulatory vessels relates to the enhanced efficacy at low dosages of the medicament treatment described herein, where the term "low" is used relative to standard peroral dosages at the levels prescribed for disorders being treated with the present method embodiments.

It has been discovered that a method of novel transnasal delivery of one or more of CBD, Dimethyltryptamine (DMT), Psilocybin, Δ8-tetrahydrocannabinol, and Δ9-tetrahydrocannabinol, at low dosage may be effective for treating, by alleviating symptoms of, neurological and/or psychological disorders. In view of this, transnasal delivery of one or more of CBD, Dimethyltryptamine (DMT), Psilocybin, Δ8-tetrahydrocannabinol, and Δ9-tetrahydrocannabinol, targeted to the SPG, is expected to be effective in the treatment of other conditions where each respective material or combination thereof is known in the art to have therapeutic benefit, but at an unexpectedly higher efficacy at the same or lower dosages than required in the oral ingestion, topical/transdermal application (including nasal sprays) and/or inhaled (vaped/smoked) regimes described in the art (e.g., clinical studies known in the art, FDA-approved regimens, and/or other published treatment regimens), where a specific therapeutically effective amount for said lower dosages may readily be determined for a given patient or given patient population through routine but not undue experimentation, well within the skill in the art as informed by the present disclosure.

By way of non-limiting background and illustration, CBD has been widely reported to have efficacy in treating the conditions identified, although it and the other medicament materials identified here are not being presented as having undergone formal clinical trials. Each of the identified medicaments also has reported efficacy in treating various ailments and disorders. See, for example, Lowe H, Toyang N, Steele B, Valentine H, Grant J, Ali A, Ngwa W, Gordon L. *The Therapeutic Potential of Psilocybin*. Molecules. 2021 May 15; 26(10):2948. doi: 10.3390/molecules26102948. PMID: 34063505; PMCID: PMC8156539; Więckiewicz G, Stokłosa I, Piegza M, Gorczyca P, Pudlo R. *Lysergic Acid Diethylamide, Psilocybin and Dimethyltryptamine in Depression Treatment: A Systematic Review*. Pharmaceuticals (Basel). 2021 Aug. 12; 14 (8): 793. doi: 10.3390/ph14080793. PMID: 34451890; PMCID: PMC8399008; Schier A R, Ribeiro N P, Silva A C, Hallak J E, Crippa J A, Nardi A E, Zuardi A W. *Cannabidiol, a Cannabis sativa constituent, as an anxiolytic drug*. Braz J Psychiatry. 2012 June; 34 Suppl 1: S104-10. English, Portuguese. doi: 10.1590/s1516-44462012000500008. PMID: 22729452; Kruger J S, Kruger D J. *Delta-8-THC: Delta-9-THC's nicer younger sibling*? J *Cannabis* Res. 2022 Jan. 4; 4 (1): 4. doi: 10.1186/s42238-021-00115-8. PMID: 34980292; PMCID: PMC8725316.

Even though the inventor predicts this efficacy based upon direct observational experience, it is based upon the highly unexpected result of effective treatment at a fraction of the known oral dosages merely by anatomically targeting delivery to the SPG without chemically altering the active ingredient, and without complexing it with—for example—a receptor-specific moiety or other modification. As such, those of skill in the art would not generally have expected/predicted therapeutic efficacy of one or more of CBD, Dimethyltryptamine (DMT), Psilocybin, Δ8-tetrahydrocannabinol, and Δ9-tetrahydrocannabinol, at lower dosages than known/characterized in clinical data and the published state of the art, but—in view of the present disclosure—those of skill in the art may now be taught to use the novel and elegant methods described herein to provide effective therapies using the medicament(s) identified but at lower dosages, via targeted delivery to the SPG.

For example, CBD administered at a concentration of 20 mg/mL has been found effective (in a study of 50 patients) to reduce self-reported anxiety and self-reported depression, to improve self-reported quality of sleep, and to improve self-reported energy level, each assessed by standard physician questionnaire during and after treatment for at least two weeks in 92% of patients and up to four weeks. This is more highly effective than administration of the same material using a nasal spray of the same concentration, which is believed to be due to the interaction of the CBD with the SPG and/or the more-highly vascularized adjacent tissues, as well as the targeted nature of delivery, which does not lose delivered material to nasal and post-nasal drainage and/or interaction with other bodily surfaces.

Specifically, CBD (in an emulsion, suspension, mixture, and/or aqueous solution) may be delivered transnasally to/toward the SPG. The method used in the study noted above delivered 0.5 mL through each nostril of a 20 mg/mL solution of CBD in an emulsified carrier of aqueous saline, medium-chain triglyceride (MCT) oil derived from coconut, lecithin (as a naturally-derived emulsifier), and potassium sorbate (as an inactive ingredient present as a stabilizer/preservative). This delivery could be effected by using a swab, injection needle, or other injection device, but more preferably and safely is effected using a transnasal injector device and methods disclosed herein and/or in one or more of U.S. Pat. Nos. 8,231,588; 8,690,839; 8,876,794; and 8,905,980, each of which is incorporated by reference herein in its entirety, and each of which is owned by the present inventor. Within the scope of the present disclosure, it is most preferable that the CBD or any effective variant or derivative thereof is administered without co-delivery of any other medicament. Co-delivery of CBD or effective derivative thereof with other medicaments, and/or at dosage levels, as characterized in other publications is not the subject of the present disclosure, and is expressly excluded from the presently claimed matter. However, delivery of the relatively low-dosage CBD or effective variant or derivative thereof described herein that includes previously undescribed co-delivered medicaments may be within the scope of certain present embodiments and claims. As such, in view of the present application, it should be understood that the methods described herein can be used with one or more of CBD, Dimethyltryptamine (DMT), Psilocybin, Δ8-tetrahydrocannabinol, and Δ9-tetrahydrocannabinol.

This method may specifically use a therapeutically effective amount of a non-prescription pharmaceutical compound according to Formula I noted above, as well as any derivatives or variants thereof that have the same physiological effect. The same regimen may be used with one or more of CBD, Dimethyltryptamine (DMT), Psilocybin, Δ8-tetrahydrocannabinol, and Δ9-tetrahydrocannabinol, where the amount to be used is initially set at one tenth of an amount known from extant literature to be effective for a specific indication, and then adjusted upward to accommodate a particular recipient's needs and responsiveness.

The therapeutically effective amount may be between about 1 mg and about 60 mg, administered once to twice per month. Effective dosage will include from about 1 mg to about 40 mg, administered as frequently as once per week to once per six weeks to two months. One effective regimen will include transnasally administering 20 mg once per two weeks (optimally delivered at 10 mg per nostril, based upon available data). Effective dosage may include transnasally administering up to 60 mg of CBD, with an effective transnasal dosage range expected to include at least 1 mg to 40 mg, expressly including each and every dosage level therebetween as well as any and all subranges thereof, where effective dosage may vary depending upon the patient and the specific indication being treated. As known for treatment regimens using CBD, dosage may remain level through multiple administrations over a period of days, weeks, months, etc., or the dosage may be increased or decreased in keeping with the therapeutic efficacy and incidence—if any—of side effects, under the guidance and supervision of a physician. In certain preferred embodiments, the effective amount is in an aqueous solution or suspension of about 0.1 mL to about 1 mL of total volume, although the volume may be up to about 5 mL. In one method, about one-half of the solution is delivered to the SPG via a right nostril of a patient, and the remaining solution is delivered to the SPG via the left nostril of the patient. In other methods, a first portion of the complete dosage may be delivered to one nostril, and a second portion (preferably completing a complete dosage) may be delivered to the other nostril.

The solubility of CBD in water is known to be very low because it is extracted as a hydrophobic oil, but combined with emulsifiers, it can be soluble in water. Although, technically, it is not so much soluble as that it appears soluble due to formation of micro-emulsion, nano-emulsion and/or liposomes with carrier oil and/or emulsifier and/or surfactant(s) such as, by way of nonlimiting example, lecithin, saponin (e.g., derived naturally from Quillaja), olive oil, coconut oil, MCT oil. Methods of preparation may include obtaining CBD in solution or suspension form. These methods will provide for easily-obtainable CBD from existing dosage forms configured for oral ingestion. The CBD may be delivered as a monotherapy, or it may be used as an adjunctive therapy with other active or inactive agents. As such, one or more of CBD, Dimethyltryptamine (DMT), Psilocybin, Δ8-tetrahydrocannabinol, and Δ9-tetrahydrocannabinol may be used.

While neither being bound by any particular theory, nor intending to affect in any measure the scope of the appended claims or their equivalents, the following background information is provided regarding present-day understanding of the anatomy of the SPG in order to further elucidate the description of the devices and methods provided hereinbelow. The SPG (also known as the pterygopalatine ganglion) is the largest group of neurons outside the cranial cavity and lies in the pterygopalatine fossa, which is approximately 1-cm wide and approximately 2-cm high. The pterygopalatine fossa is bordered anteriorly by the posterior wall of the maxillary sinus, posteriorly by the medial plate of the pterygoid process, medially by the perpendicular plate of the palatine bone, and superiorly by the sphenoid sinus. Laterally, the pterygopalatine fossa communicates with the infratemporal fossa.

The SPG within the fossa is located posterior to the middle turbinate of the nose and lies a few millimeters (1 mm to 5 mm) deep in the lateral nasal mucosa. The SPG has a complex neural center and multiple connections. The SPG is suspended from the maxillary branch of trigeminal nerve at the pterygopalatine fossa via the pterygopalatine nerves, and lies medial to the maxillary branch when viewed in the sagittal plane. Posteriorly, the SPG is connected to the vidian nerve. The SPG itself has efferent branches and forms the superior posterior lateral nasal and pharyngeal nerves. Caudally, the ganglion (SPG) is in direct connection with the greater and lesser palatine nerves.

The SPG has sensory, motor and autonomic components. The sensory fibers arise from the maxillary nerve, pass through the SPG, and are distributed to the nasal membranes, the soft palate and some parts of the pharynx. A few motor nerves are also believed to be carried with the sensory trunks. The autonomic innervations of the SPG are more complex. The sympathetic component begins with preganglionic sympathetic fibers originating in the upper thoracic spinal cord, forming the white ramie communicates, coursing through the sympathetic ganglion, where the preganglionic fibers synapse with the postganglionic ones. The postganglionic fibers then join the carotid nerves before branching off and traveling through the deep petrosal and vidian nerves. The postganglionic sympathetic nerves continue their path through the SPG on their way to the lacrimal gland and nasal and palatine mucosa.

The SPG is usually considered parasympathetic in function. The parasympathetic component of SPG has its preganglionic origin in the superior salivatory nucleus then travels through a portion of the facial nerve (VII) before forming the greater petrosal nerve to form the vidian nerve, which ends in the SPG. Within the ganglion, the preganglionic fibers synapse with their postganglionic cells and continue on to the nasal mucosa, and one branch travels with the maxillary nerve to the lacrimal gland.

Notwithstanding the description above, and regardless of the currently-held theories respecting the anatomy of the SPG, a safe and effective treatment for at least alleviating one or more symptoms of various neurological disorders, as well as of self-reported or clinically-diagnosed depression, substandard sleep quality, appetite control issues, social anxiety, general anxiety, PTSD, traumatic memory-related stress, cluster headaches, intractable phantom-limb pain (PLP), chronic pain, and/or obsessive-compulsive disorders (OCD), can be achieved as a result of using the devices and methods described below. Although representative devices 10, 54, and 254 will be described in reference to FIGS. 1-4 and FIGS. 6-9, respectively, it is to be understood that these representative devices are merely illustrative and that alternative structures can likewise be utilized for delivering a medicament in accordance with principles described herein. It is to be understood that elements and features of the various representative devices described below may be combined in different ways to produce new embodiments that likewise fall within the scope of the present teachings. The drawings and the description below have been provided solely by way of illustration, and are not intended to limit the scope of the appended claims or their equivalents. However, this description including its claims are specifically directed to targeted delivery to the SPG by use of a low dose dispenser, which distinguishes away from general application as used with nasal sprays, inhalers, and/or topical application of medicament with a swab or other mechanical device providing physical contact with the tissue around the SPG.

Figure 3:
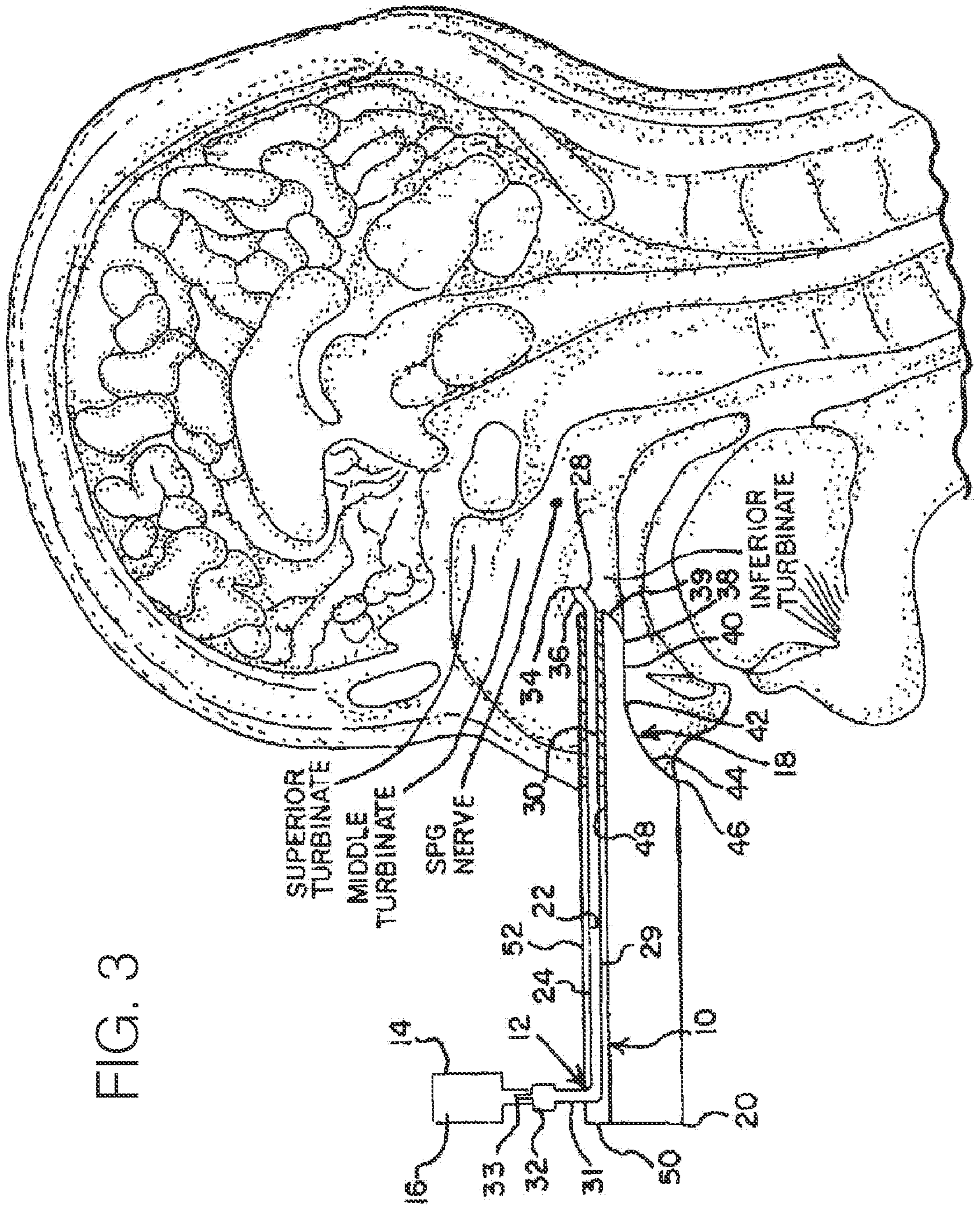
FIG. 3 shows a cross-sectional side view of the device of FIG. 1 after the introducer has been engaged with a patient's nostril in accordance with principles described herein.
Figure 4:
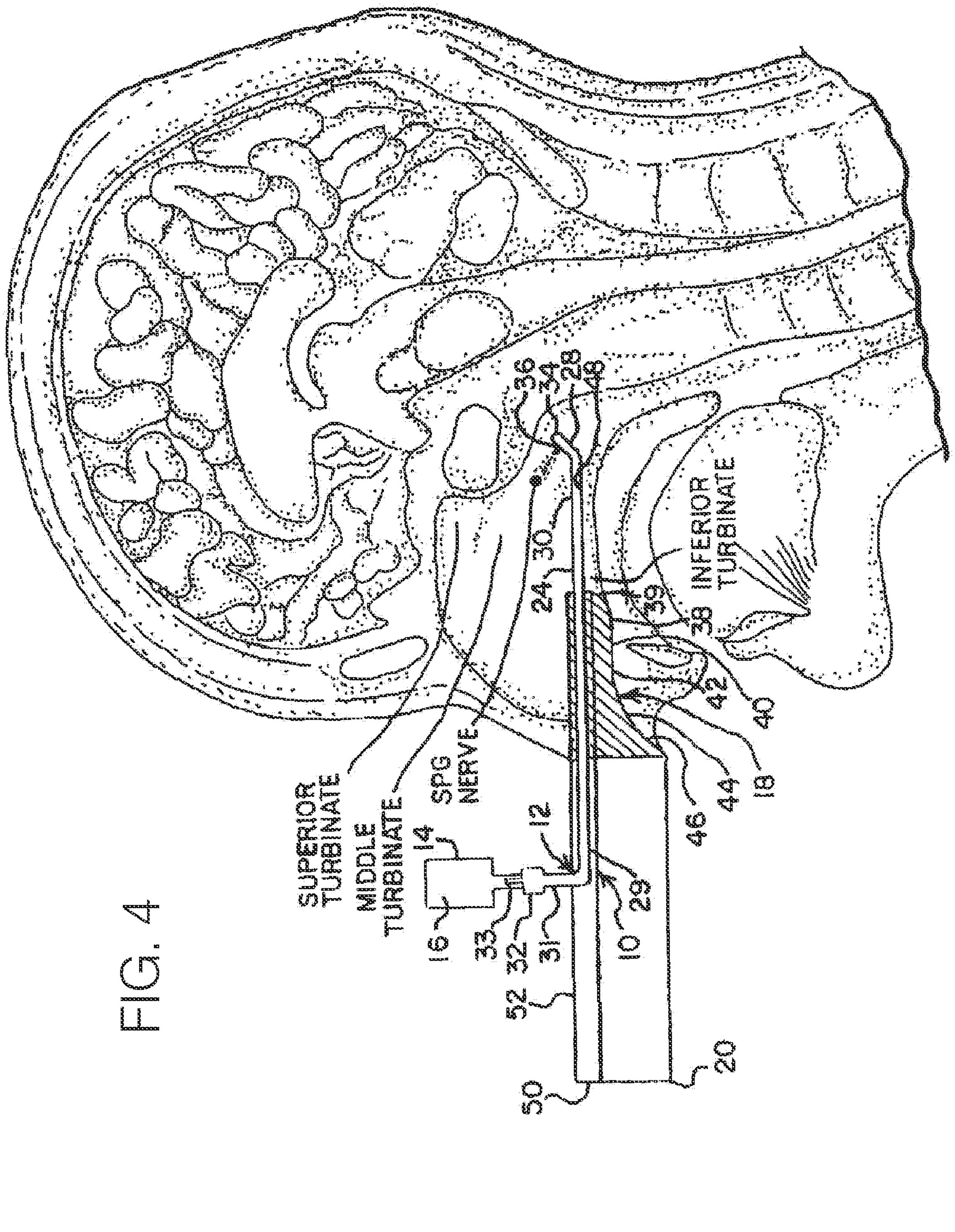
FIG. 4 shows a cross-sectional side view of the device of FIG. 1 after the introducer has been engaged with a patient's nostril and after the injector has been moved from its storage position to an engaging position that positions the second end of the injector medial, posterior, and inferior to the sphenopalatine ganglion.
Figure 5:
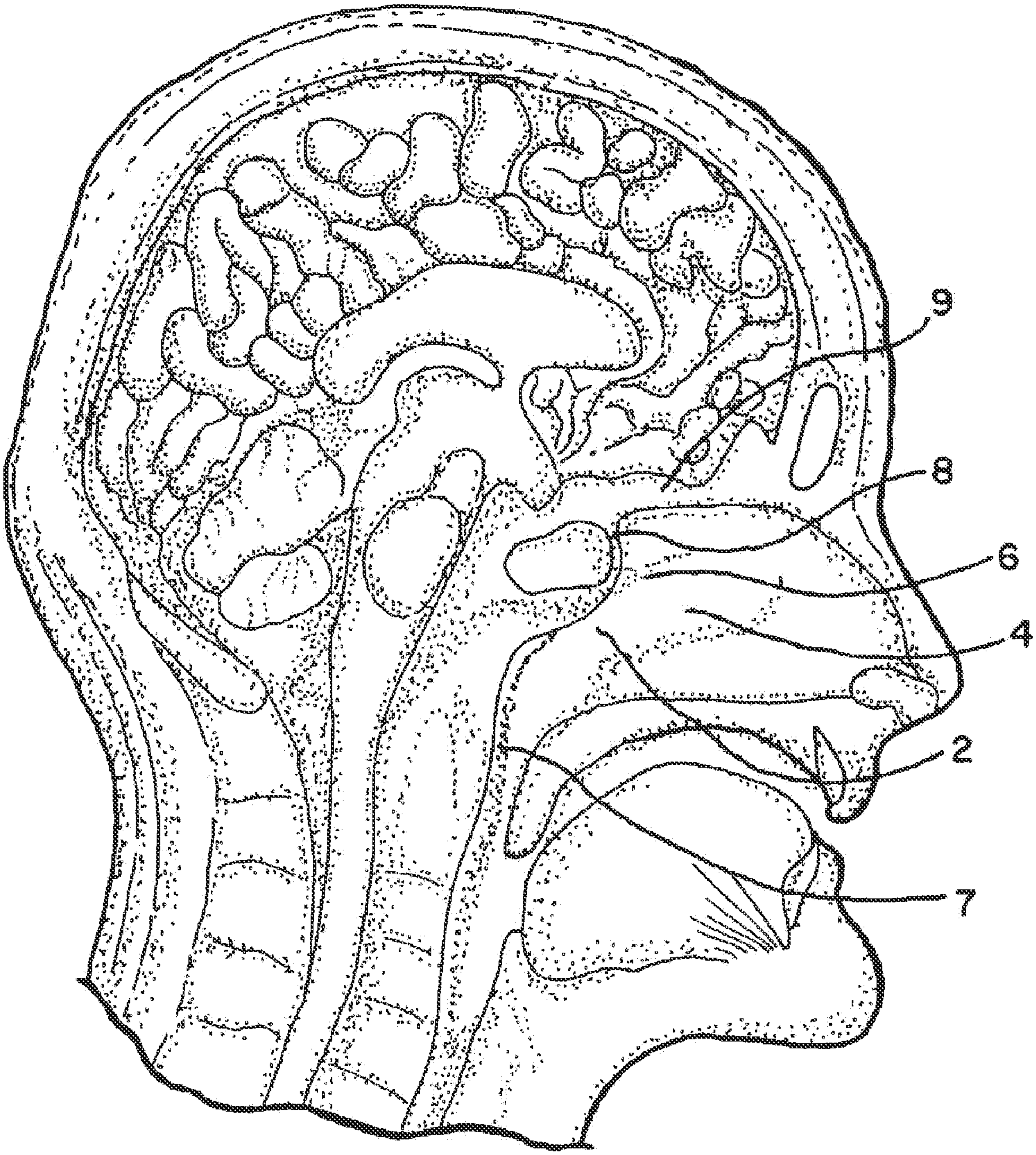
FIG. 5 shows a median cross-sectional view of a human head with the SPG shown in its correct anatomical position posterior to the middle turbinate.

FIGS. 1-4 show a representative device 10 for delivering a medicament to a patient in need thereof. The device 10 includes an injector 12 comprising a first end 29 configured to remain outside a nasal passage of the patient and a second end 30 configured for entry into the nasal passage of the patient. Device 10 further includes an introducer 18 configured for engagement with a nostril of the patient and comprising a passageway 48 configured for slidably receiving the injector 12. The injector 12 is moveable between a storage position (best shown by FIG. 1) preceding engagement of introducer 18 with a patient's nostril, and an engaging position (best shown by FIG. 4) pursuant to engagement of introducer 18 with the patient's nostril. However, upon the initial engagement of introducer 18 with a patient's nostril, the injector 12 is desirably maintained—at least for a time—in a storage position (best shown by FIG. 3) until it is deliberately moved to an engaging position (best shown by FIG. 4) under the direction of a user. In some embodiments, the engaging position of injector 12 is situated medial and/or inferior to the SPG. In other embodiments, the engaging position of injector 12 is situated medial, inferior, and posterior to the SPG, as best shown by FIG. 4.

As used herein, the phrases "storage position" and "engaging position" are each intended to encompass multiple positions within a selected range. For example, in some embodiments, the degree to which injector 12 is extended into the nostril of a first patient (e.g., a child) will vary from the degree to which injector 12 is extended into the nostril of a second patient (e.g., an adult male). Notwithstanding, the phrase "engaging position" is intended to encompass many variations in the precise position of injector 12 within the nostril, any of which are properly regarded as being medial and/or posterior and/or inferior to the SPG. In some embodiments, injector 12 is not slidable within introducer 18 but rather is fixed in a predetermined position so as to be medial and/or inferior to the SPG upon engagement of introducer 18 with a patient's nostril. In other embodiments, injector 12 is not slidable within introducer 18 but rather is fixed in a predetermined position so as to be medial, posterior, and inferior to the SPG upon engagement of introducer 18 with a patient's nostril.

The injector 12 comprises a tubular section 24 (a so-called cobra tube in recognition of the tube's extensibility) that includes a channel 22 extending from first end 29 to second end 30 and configured for receiving a medicament. In some embodiments, tubular section 24 has an outer diameter of about 5 mm and channel 22 has an inner diameter of about 2 mm. Throughout this description, measurements and distances such as the diameters just given are to be strictly regarded as being merely representative and in no way limiting and/or fixed. Considerable variation in all measurements and distances provided in this description is possible, as will be readily appreciated by one of ordinary skill in the art.

In some embodiments, the second end 30 of injector 12 contains a nozzle 28 having a tip 34 that contains one or a plurality of apertures 36 configured for spraying a medicament superiorly and/or laterally and/or anteriorly towards the SPG. In some embodiments, nozzle 28 is configured for spraying a medicament laterally and/or superiorly towards the SPG, and in other embodiments, nozzle 28 is configured for spraying a medicament laterally, superiorly, and anteriorly towards the SPG. Spraying includes directing in a stream, mist, or anything in between, subject to the size/shape of the delivery aperture, viscosity of the liquid being delivered, and the pressure administered thereto. Most preferably, and to maintain efficacy and efficiency with regard to targeting the SPG and delivering a smallest effective dose, the spray is directed laterally and/or superiorly, and anteriorly, but not posteriorly.

In some embodiments, nozzle 28 extends at an upward angle of inclination from second end 30 of injector 12. In some embodiments, nozzle 28 extends in a lateral, anterior, and superior direction at an angle of inclination ranging from about 45 degrees to about 60 degrees to accommodate varying patient anatomies in which the SPG resides in a lateral cave posterior to the middle turbinate. In some embodiments, nozzle 28 has a length ranging from about 2 mm to about 5 mm. In some embodiments, injector 12 is designed to exhibit handedness, such that in some embodiments, injector 12 is configured for engagement with a left-side nostril of a patient, whereas in other embodiments, injector 12 is configured for engagement with a right-side nostril of the patient (with the contour of a left-handed injector being generally complementary to the contour of a right-handed injector).

The introducer 18 can be aimed into a nostril to provide a horizontal pathway substantially parallel to the bottom of the nasal cavity or floor of the nose—such that introducer 18 is supported on the bottom of the nasal cavity—to a position medial to the inferior turbinate. This self-seating feature of introducer 18 facilitates quick and accurate usage by a patient without necessitating supervision from a medical professional. In some embodiments, introducer 18 provides an extended pathway of between about 1.5 cm and about 2 cm into the nostril. Once introducer 18 is placed firmly against the nose, the tip of the nose will tend to point superiorly. The tubular section 24 of injector 12 can then be pushed partially or completely into the back of the nostril. In order to accommodate the slightly curved nature of the interior anatomy of the nose, the passageway 48 in which tubular section 24 lies can be curved slightly to the ipsilateral nostril by about 5 to about 20 degrees. Once tubular section 24 is in position, a medicament can then be delivered to the SPG from nozzle 28 to exert the desired SPG blocking effect. In some embodiments, device 10 is provided with an optional safety abutment stop to limit the extent of travel into the nostril available to injector 12.

As best shown by FIGS. 1, 3, and 4, introducer 18 contains a first portion 44 and a second portion 38. In some embodiments, a cross-sectional area of first portion 44 is larger than a cross-sectional area of second portion 38. In some embodiments, first portion 44 is generally concave and has a contour 46 configured to be complementary in shape to an interior of the nostril so as to substantially conform therewith. In some embodiments, narrow second portion 38 has a rounded convex portion 39 and an underside 40 having a generally flat surface 42. The passageway 48 of introducer 18 slidably receives tubular section 24 of injector 12 and, in some embodiments, has a diameter of between about 6 mm and about 7 mm. In some embodiments, second portion 38 of introducer 18 contains a nostril-engaging tip that extends from about 1 cm to about 3 cm. In some embodiments, first portion 44 of introducer 18 extends from about 2 cm to about 3 cm. In some embodiments, introducer 18 is designed to exhibit handedness, such that in some embodiments, introducer 18 is configured for engagement with a left-side nostril of a patient, whereas in other embodiments, introducer 18 is configured for engagement with a right-side nostril of the patient (with the contour of a left-handed introducer being generally complementary to the contour of a right-handed introducer).

In some embodiments, device 10 further includes a container 14 in communication with first end 29 and channel 22 of injector 12, which is configured for holding a medicament 16 (e.g., CBD, and/or any of the other medicaments identified herein, including any effective variants and/or derivatives thereof). In some embodiments, as shown in FIGS. 1, 3, and 4, container 14 is supported on a stem 26 having a lower section 31 which, in some embodiments, has an outer diameter substantially the same as that of tubular section 24. Lower section 31 can extend outwardly and/or upwardly and/or at an angle of inclination from first end 29 of injector 12 and, in some embodiments, connects with an upper section 32 having an enlarged diameter configured to receive an outlet 33 of container 14. Analogous to lower section 31, upper section 32 can extend outwardly and/or upwardly and/or at an angle of inclination.

In some embodiments, container 14 is operatively connected, mounted or otherwise secured to upper stem section 32 and is fully or partially filled with a medicament 16. Since container 14 is in communication with channel 22 of injector 12, medicament 16 can be delivered along tubular section 24 and released through one or more apertures 36 of nozzle 28. Container 14 can be formed of plastic, metal or the like, and can be squeezable and/or pressurized to facilitate medicament delivery into channel 22. In some embodiments, container 14 is replaced by a port (not shown), such that a medicament can be introduced through the port into upper section 32 by a delivery device such as a syringe.

In some embodiments, device 10 further includes an optional handle 20 connected to a rear portion of introducer 18 adjacent first portion 44. The handle 20 includes an upwardly facing groove 50 that provides a track 52 configured to receive and in communication with passageway 48 of introducer 18 to slidably receive tubular section 24 of injector 12. In some embodiments, track 52 has a depth or width of between about 6 mm and about 7 mm. Handle 20 is configured for movement towards a patient's face, such that posterior movement of handle 20 moves introducer 18 into engagement with the nostril of the patient.

Injector 12, introducer 18, and handle 20 can be formed from all manner of materials including but not limited to flexible, rigid or semi-rigid polymeric materials (e.g., plastics, rubbers, etc.), metals and alloys thereof, and the like, and combinations thereof. In some embodiments, injector 12 is formed of a flexible plastic, introducer 18 is formed of an elastomeric and/or resilient plastic or rubber, and handle 20 is formed of plastic. In some embodiments, one or more of injector 12, introducer 18, and handle 20 is designed from a material so as to be disposable and/or biodegradable.

While the representative device 10 described above can be used to deliver a medicament superiorly and/or laterally and/or anteriorly towards a sphenopalatine ganglion of a patient in accordance with the principles set forth herein, alternative structures can likewise be employed to similarly accomplish such a delivery. For example, an injector device may include a configuration like that shown in FIG. 8, but without need for deployment, positionable for medicament delivery in the manner shown in FIG. 4. Such a device and method are contemplated herein and subject to the present claims.

By way of illustrative but non-limiting example, a delivery tube having a curved portion at one of its ends configured for insertion into a patient's nostril—analogous to the angled nozzle 28 provided on the second end 30 of injector 12—can be housed within a substantially cylindrical (e.g., pen- or cigar-shaped) housing. The delivery tube can be formed of a flexible or semi-rigid material (such as a plastic) such that it can be maintained in a substantially linear or non-curved arrangement while in its storage position within the housing but readily restored to its curved configuration when extended from the housing into an engaging position. In such a device, one or more internal surfaces of the external housing acts to straighten or restrain—completely or at least partially—the inherent curvature of the delivery tube until such time as the delivery tube is moved to an engaging position, whereupon the curvature of the tube is restored. In some embodiments, at least a portion of the delivery tube (e.g., the end designed to emit medicament) can be expandable if desired (e.g., when air, oxygen and/or other gases, and/or medicaments are forced through the tube under pressure).

By providing one or more optional indicial markings on the cylindrical housing described above, a user can readily identify the direction of curvature of the delivery tube stored inside, such that by turning the housing around and arc of 360 degrees, the user can select any desired direction of spray for delivering a medicament through the delivery tube. Simply by rotating the housing, the direction of spray can be incrementally changed through a continuous arc between 0 degrees and 360 degrees inclusive. In design, one end of the housing can be fitted with a Luer lock configured to engage with a syringe containing the medicament. Alternatively, the end of the housing configured to remain outside the nostril can be fitted with a septum or similar such membrane through which a medicament can be introduced into the delivery tube housed therein.

Numerous other modifications to the delivery devices described herein, as well as alternative structures, are likewise contemplated for use to the extent they similarly allow for the delivery of a medicament superiorly and/or laterally and/or anteriorly towards a sphenopalatine ganglion of a patient in accordance with the present teachings. By way of example, the portion of the device configured for insertion into a patient's nostril (e.g., a portion of the injector 12 described above) can be formed from any therapeutically acceptable malleable material (e.g., plastics, metals, metal alloys, and the like) capable of receiving and retaining a desired shape when manipulated by a user. (e.g., increased or decreased curvature of the angled nozzle 28 provided on the second end 30 of injector 12). Such a feature may be desirable, for example, when a clinician wishes to customize the exact geometry of a device before using it on a patient in a clinical setting.

FIGS. 6-9 show a representative device 54 for delivering a medicament to a patient in need thereof. The device 54 includes an injector 56 comprising a first end 58 configured to remain outside a nasal passage of the patient and a second end 60 configured for entry into the nasal passage of the patient. Device 54 further includes an introducer 62 configured for engagement with a nostril of the patient and comprising a passageway 64 configured for slidably receiving the injector 56. The injector 56 is moveable between a storage position (best shown by FIGS. 6 and 7) preceding engagement of introducer 62 with a patient's nostril, and an engaging position (best shown by FIG. 8) pursuant to engagement of introducer 62 with the patient's nostril. It should be appreciated with reference to this illustration that a syringe or other medicament-containing/medicament-delivering device would be at least partially received into the passageway 64 as a means of (or result of) advancing the injector distally relative to the introducer. Such a device preferably is attached to and in patent fluid communication with the injector tube lumen.

Figure 8:
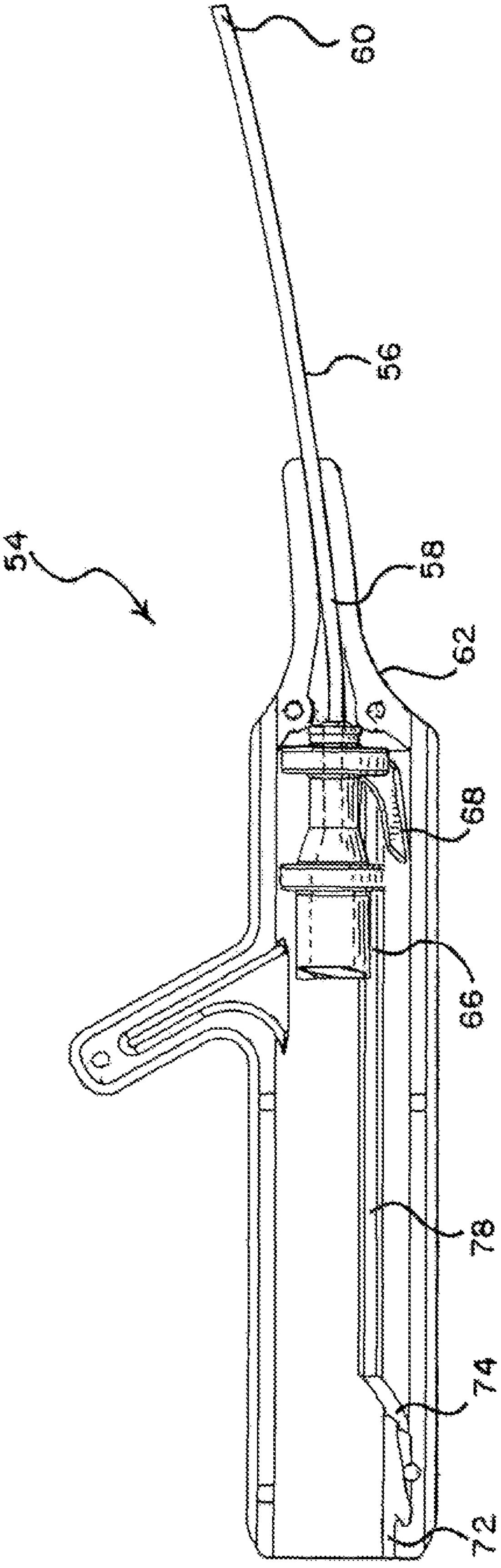
FIG. 8 shows a partial cross-sectional side view of the device of FIG. 6 with the injector in an engaging position.
Figure 9:
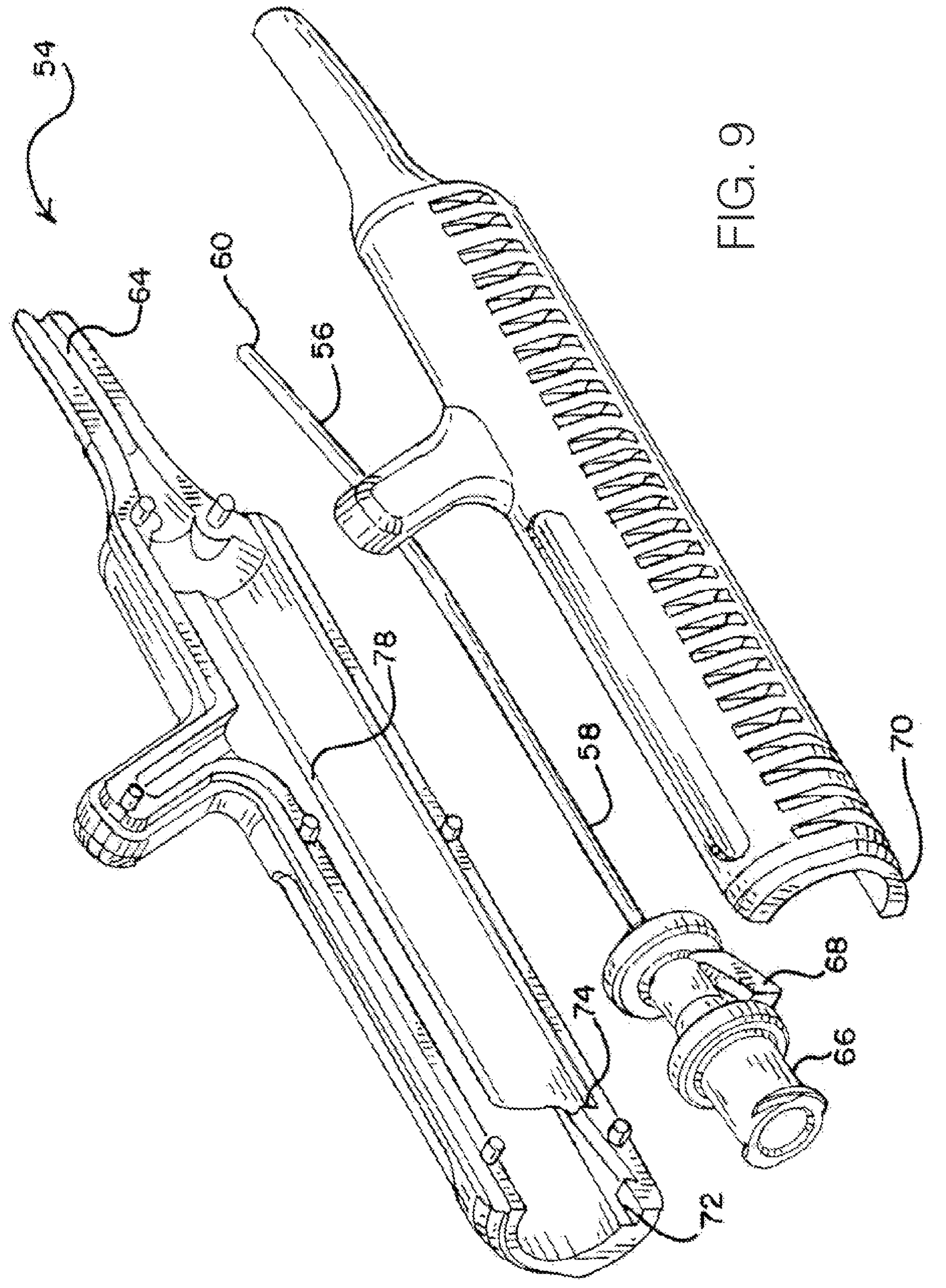
FIG. 9 shows an exploded perspective view of the device of FIG. 6.

As shown by FIGS. 6 and 7 (see also FIGS. 11-11B), the injector 56 (256) may be coupled to a hub 66 fitted with a Luer lock mechanism configured to engage with the threads of a syringe (not shown) containing a medicament to be delivered to a patient. As best shown by FIGS. 7-9, the hub 66 is coupled to a stop bar 68 that is compressible. Prior to engagement with a syringe, hub 66 is configured to remain outside of housing 70 and to resist rotation therein since stop bar 68 is positioned within a keyed slot 72 formed by the two halves of housing 70. As hub 66 is pressed axially into housing 70 (e.g., by a syringe coupled to the Luer lock mechanism on hub 66), stop bar 68 travels along keyed slot 72 until it reaches lip 74 at which point stop bar 68 engages lip 74, thereby preventing retraction of hub 66 from the interior of housing 70, and at which point hub 66 (and the syringe coupled thereto) become rotatable over a fixed range. The irreversibility of the axial travel of hub 66 within housing 70 provides a useful way for a practitioner to readily distinguish a used device from an unused one—namely, if hub 66 does not protrude from housing 70, the device has previously been used.

As may best be understood from a consideration of FIGS. 8 and 9, stop bar 68 is further configured to act in conjunction with a ledge 78 inside of housing 70 such that the range of rotation of hub 66 (and the syringe coupled thereto) is limited to predetermined angles (e.g., about 45° clockwise or 45° counterclockwise). Rotation beyond the predetermined angles (which are determined based on positioning of ledge 78) is prevented when stop bar 68 butts up against ledge 78. This feature facilitates accuracy of use by a user by limiting the positions from which medicament can be introduced from injector 56 to those having the desired trajectory towards a target site.

As best shown by FIG. 8, injector 56—which in some embodiments comprises a flexible plastic tube having shape memory—retains a slight curvature that is conferred upon it by the curved portion of the lumen 64 of the distal end of the introducer 62 during storage. By virtue of this curvature, and by providing one or a plurality of apertures along the side of second end 60, the injector 56 is designed to be used in both the left-side and right-side nostrils of a patient without regard to handedness (see, by way of illustration, aperture 236 in FIG. 11B).

In some embodiments, the diameter of the one or plurality of apertures along the side of second end 60 of injector 56 is smaller than an outer diameter of the flexible plastic tube, such that the liquid expelled through the aperture upon pressing the plunger of the syringe exits forcefully. In some embodiments, depending on the flexibility of the plastic tube, injector 56 undergoes further curvature under the pressure exerted by depression of the syringe plunger (e.g., in a direction away from that of the liquid exiting the aperture). In some embodiments, the diameter of the one or plurality of apertures is smaller than an inner diameter of the flexible plastic tube. In some embodiments, the flexible plastic tube comprises a nylon resin (e.g., such as that sold under the tradename PEBAX 72D). In some embodiments, the flexible plastic tube comprises PEBAX 72D, has an outer diameter ϕ of 0.039.+-. 0.001, has a wall thickness of 0.005.+-0.0.001 (i.e., five thousandths of an inch), and has an aperture with a diameter of 0.005.+-. 0.001. In some embodiments, the aperture is oriented at a 50° angle in a direction oriented towards the hub. In some embodiments, introducer 62, housing 70, keyed slot 72, lip 74, and ledge 78 are integrally formed (in some embodiments, as two complementary molded halves press fit and/or bonded together, such as with adhesives, sonic welding or the like) and, in some embodiments, these portions comprise polycarbonate. In some embodiments, hub 66 and stop bar 68 likewise comprise polycarbonate.

A method for treating a patient in accordance with the present teachings includes delivering a medicament superiorly and/or laterally and/or anteriorly towards a sphenopalatine ganglion of a patient using a device as described herein. In some embodiments, the medicament is delivered laterally and/or superiorly towards the SPG. In other embodiments, the medicament is delivered laterally, superiorly, and anteriorly towards the SPG.

In some embodiments, a method for treating a patient includes (a) introducing an injector 12 through a nasal passage of the patient into a region substantially medial and/or posterior and/or inferior to an SPG of the patient; and (b) delivering a medicament from injector 12 superiorly and/or laterally and/or anteriorly towards the SPG. In some embodiments, injector 12 is introduced through a nasal passage of the patient into a region substantially medial and/or inferior to the SPG, whereas in other embodiments the injector 12 is introduced into a region substantially medial, inferior, and posterior to the SPG. In some embodiments, the medicament is delivered laterally and/or superiorly towards the SPG, whereas in other embodiments, the medicament is delivered laterally, superiorly, and anteriorly towards the SPG. In some embodiments, injector 12 has a second end 30 containing one or a plurality of apertures 36 through which a medicament is sprayed towards the SPG.

In some embodiments, injector 12 is slidably received in an introducer 18, as described above, and the method further includes (c) engaging introducer 18 with a nostril of the patient, such that a portion of the patient's nose is lifted upon engagement with introducer 18; and (d) sliding injector 12 from a storage position to an engaging position after introducer 18 is engaged with the nostril. As described above, the engaging position of injector 12 is situated medial and/or posterior and/or inferior to the SPG-medial and/or inferior in some embodiments, and medial, inferior, and posterior in other embodiments. In some embodiments, the medicament is provided in a container 14 connected to and in communication with injector 12, as described above, and the method further includes (e) squeezing container 14 containing the medicament in order to spray the medicament towards the SPG.

In some embodiments, the method includes pushing introducer 18 snugly and comfortably within a nostril to lift the tip of the patient's nose before positioning the nozzle 28 of injector 12 in proximity to the SPG, sliding tubular section 24 of injector 12 through passageway 48 in introducer 18, and/or sliding tubular section 24 of injector 12 on a track 52 of handle 20. This method for transnasally delivering a medicament will be understood by those of skill in the art with reference to FIGS. 1, 3, and 4 by way of anatomic reference, as well as the other figures showing device embodiments, elements of each of which can be combined and/or interchanged with each other, where those of skill in the art will readily appreciate the device construction and variants as well as the methods of delivery with reference to the present disclosure.

FIGS. 10-12B show elements of another device embodiment 254, which assembles in substantially the same manner as the device 54 shown in FIGS. 6-9, and which device 254 includes an injector 256 (including a hub 266) and an introducer 262, and which may also include (when assembled for use in delivering medicament) a medicament container embodied as a syringe 214 (that is engageable with the injector and partially receivable within the introducer). As illustrated, embodiments of the device may include a novel connector interface that provides locking functionality to provide an effectively fluid-patent engagement of the syringe 214 with the hub 266 of the injector 212. The locking engagement may provide for ensuring single-use functionality of the device (which may provide hygienic and other safety advantages).

The introducer 262 is illustrated with reference to FIGS. 10-10G, and may also be understood with reference to the structure and function described above regarding FIGS. 6-9. The introducer 262 includes an elongate generally cylindrical body wall defining a housing 270, which surrounds a lumen 271. The lumen 271 includes at least two longitudinal channels 272*a*, 272*b* parallel to each other, each channel forming a depressed track along a lumen-facing body wall surface. The longitudinal channels 272*a*, 272*b* merge to form a single channel 272 near the proximal end of the introducer 262. As shown in FIGS. 10E-10G, the channels 272, 272*a*, 272*b* may form (respectively) a goalpost shaped, a Y-shaped, or a U-shaped configuration. This channel is configured to slidingly receive the stop-bar 268 of the injector hub 266, which is embodied as a channel-engaging lateral projection near the proximal injector end (as shown in FIGS. 11A-11B).

Figure 10:
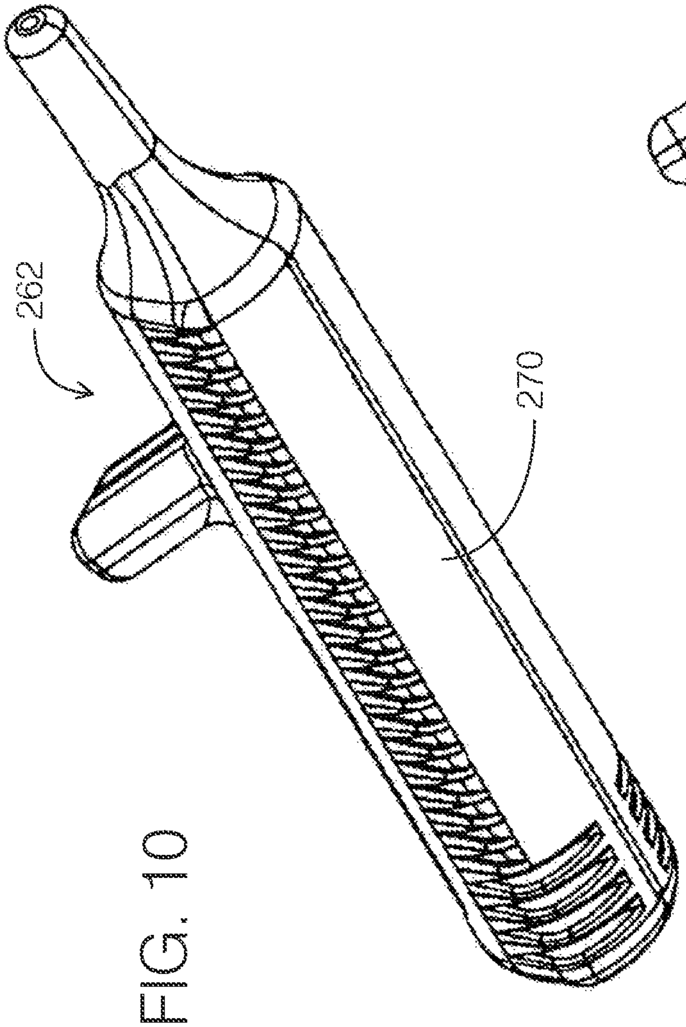
Figure 10A:
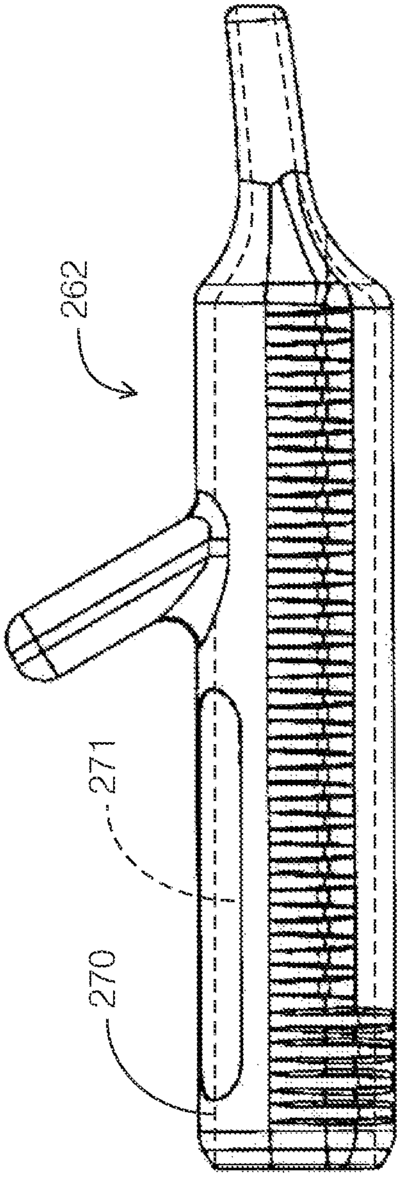
Figures 10B, 10C, 10D, 10E, 10F, 10G:
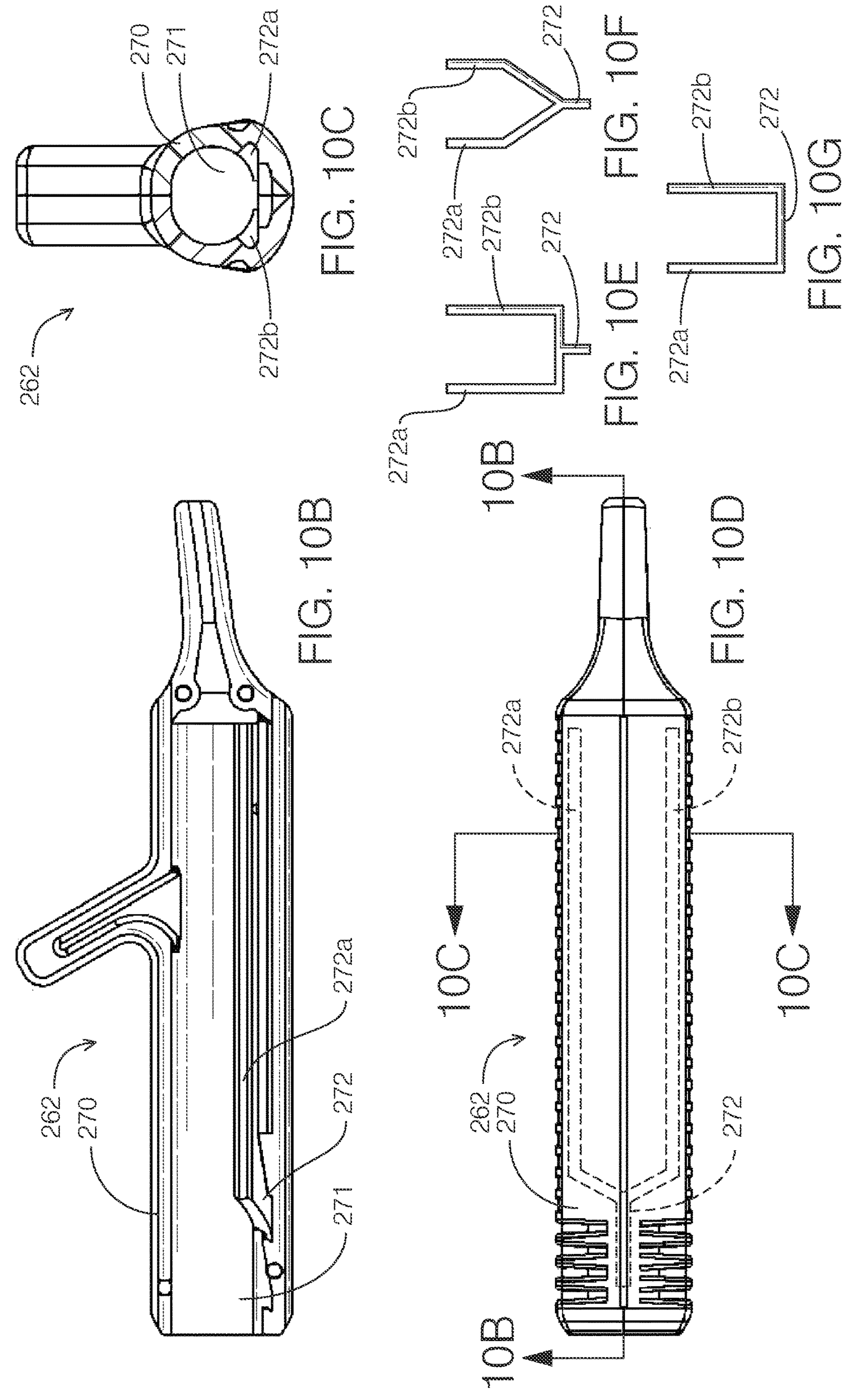

FIG. 10 shows a bottom perspective view of the introducer 262. FIG. 10A shows an external side view thereof. FIG. 10B shows a longitudinal section view along line 10B-10B of FIG. 10A, and FIG. 10C shows a transverse section view along line 10C-10C of FIG. 10D. One configuration of the channels 272, 272*a*, 272*b* is shown in FIGS. 10B-10C, and another in FIG. 10D. In particular, FIG. 10C illustrates the radial angle relative to the central longitudinal axis at which each of the channels 272*a*, 272*b* extends along a more distal length of the introducer body 270. The radial orientation of the stop bar 268 in each of the channels 272*a*, 272*b* when the stop bar 268 is distally advanced in the channel (such that the injector distal end 260 is extended out of the introducer 270 (in the same manner as shown in FIG. 8) provides for user-selectable orientation of the injector side aperture 236 toward the SPG region from each of the patient's right and left nostrils while preventing radial rotation of the injector 256 during the time it is extended into the patient's nostril.

Figure 11:
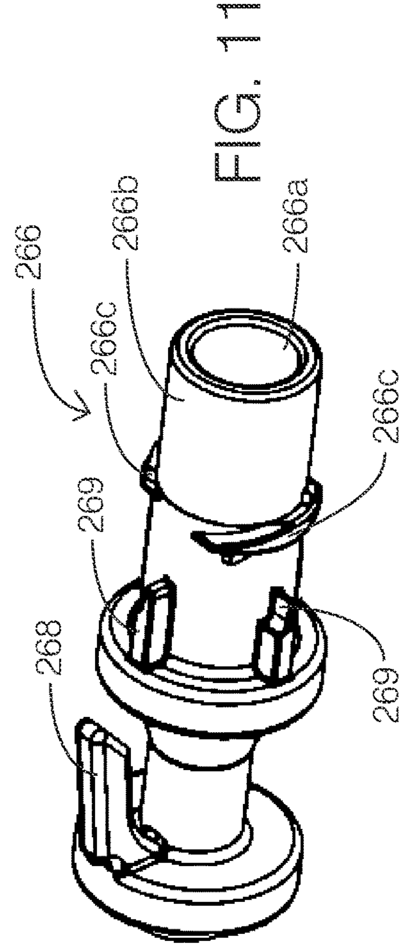
FIG. 11 shows an injector hub embodiment.
Figure 11A:
FIG. 11A shows an injector embodiment (inverted relative to the orientation in which it may enter the introducer of FIGS. 10-10A.
Figure 11B:
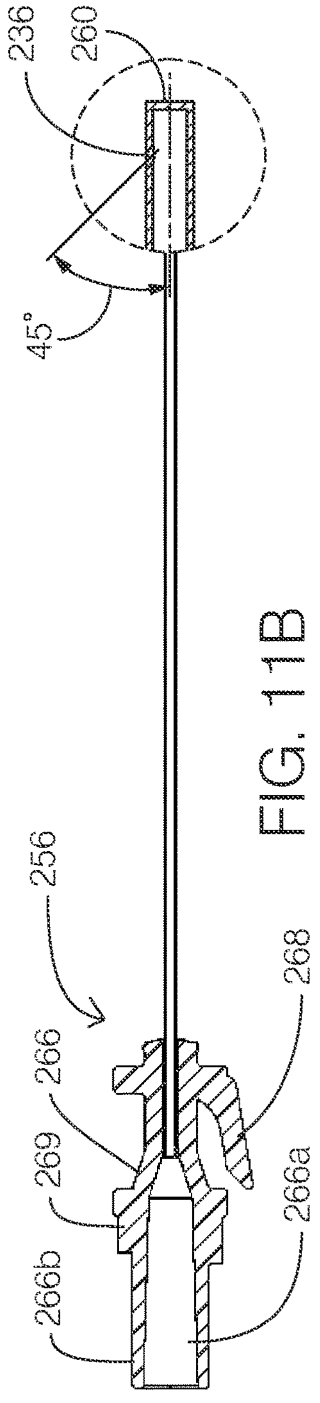
FIG. 11B shows a longitudinal section view of an injector, including a detail view of the distal end showing the side aperture thereof.

FIG. 11B shows an inverted longitudinal section view (taken along line 11B-11B of FIG. 11), with this inverted orientation provided to show how the hub would align with and engage into the introducer 262 shown in FIGS. 10-10D. As shown in the magnified distal section detail of FIG. 11B, the side aperture 236 near the distal injector end 260 preferably is coplanar with a longitudinal axis (whether straight or curved) of the injector 256 and is oriented at a non-perpendicular angle relative to that axis such that the spray proceeding out of the aperture 236 is directed somewhat proximally and upward to target the SPG region along a spray path in the manner described above. In one embodiment, the aperture 236 may have a diameter of about 0.01 inches (about 0.25 mm) and be oriented at an angle between about 30° and about 60°, preferably about 45°. This orientation preferably provides an optimum spray path access to the SPG region in the manner described above with reference to FIG. 4.

The injector 256 with its hub 266 is illustrated in FIGS. 11-11B. The hub 256 is generally cylindrical with a proximal Luer lock construction that may be made to comply with ISO standards 594-1 and 594-2. Its distal end region is configured to slidingly engage into the introducer lumen 271, with the stop bar 268 slidingly engaged into the channels 272 (and, upon actuation, a selected one of 272*a* or 272*b*). The stop bar 268 includes a weakened distal region 268*a* that is configured to fail and allow the stop bar to bend over and/or break off when subjected to a predetermined lateral force by rotation of the hub when the stop bar is engaged into a channel. The predetermined force preferably corresponds to a force required to overcome and disengage the connector interface described below (e.g., the same as or less than the rotational force required to overcome the lock between the syringe and the injector hub effected by tooth/notch and Luer lock engagement, such that connecting then disconnecting a syringe from the hub will limit its effective use to a single-use). Delivery devices of the present disclosure and kits including them may be available under the trade name Tx360® from Tian Medical (Lombard, Ill.).

Figure 12:
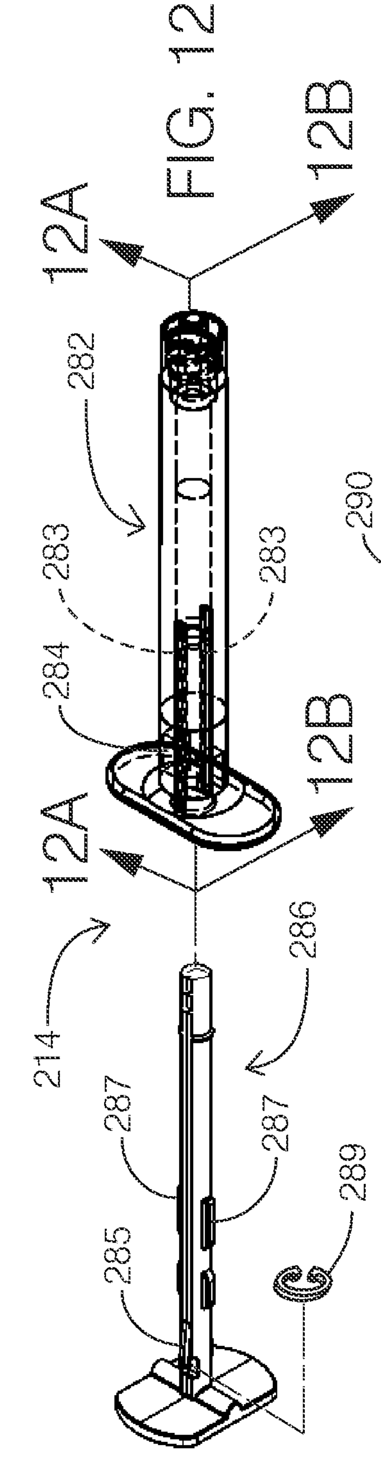
FIG. 12 shows a syringe assembly including a plunger oriented/rotated 90° relative to the barrel that receives it.
Figure 12A:
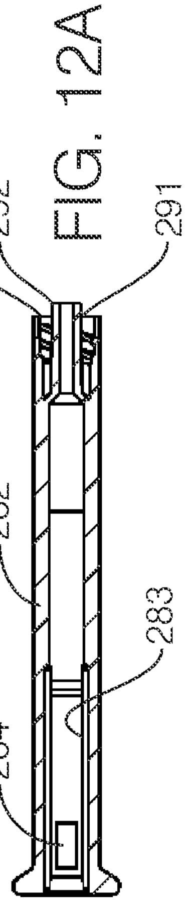
FIG. 12A shows a longitudinal section view of the syringe barrel.
Figure 12B:
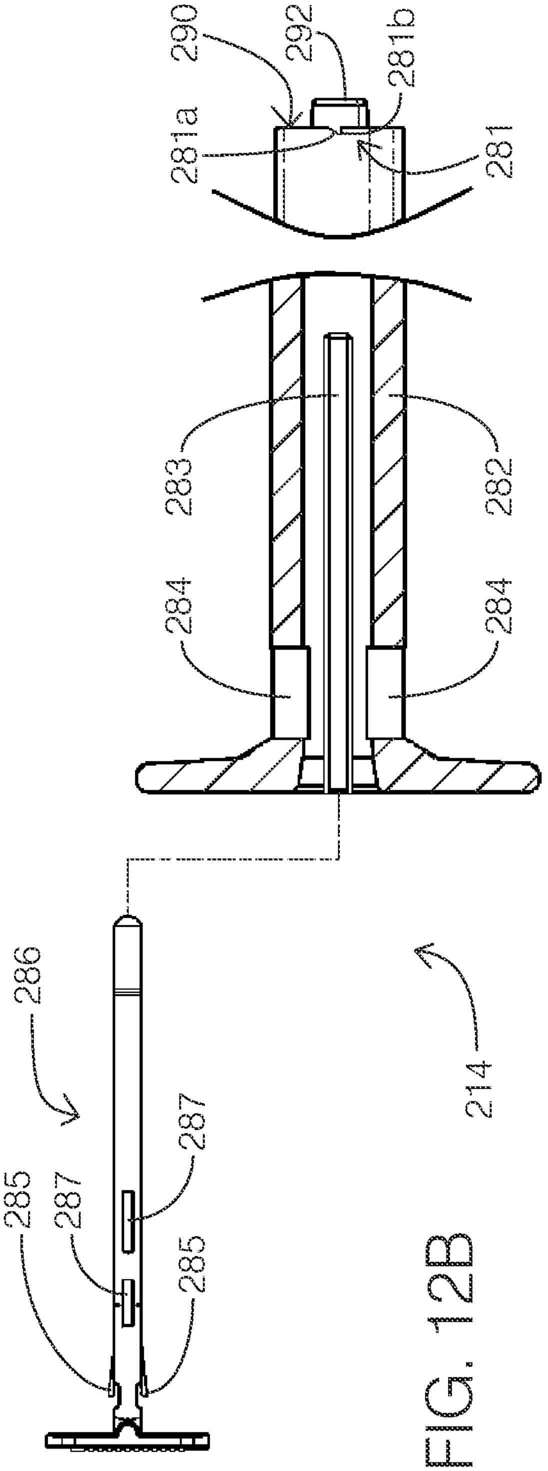
FIG. 12B shows the assembly with a different view angle of the plunger and a relatively magnified view of the barrel that receives the plunger.

FIGS. 12-12B show a syringe assembly 214, configured to participate in a connector interface with the hub 266. FIG. 12 shows a disassembled perspective view of the plunger and barrel of the syringe 214. The syringe 214 may include one or more features providing for single-use functionality. As shown in FIGS. 12A-12B, the barrel 282 includes a proximal-end longitudinal inner track 283 that engages/receives opposing laterally-protruding fins 287 of a locking plunger 286 to provide for non-rotary longitudinal plunger movement within the barrel 282. The plunger 286 also includes opposed laterally extending locking flanges 285 that engage into a pair of opposed flange-receiving windows 284 in the barrel 282 when the plunger 286 is fully advanced into the barrel. This prevents withdrawal of the plunger 286 from the barrel 282 as one means of promoting single-use-only of the device. A spacer 289 may be provided to clip around the base of the plunger 286 and prevent inadvertent flange/window locking before the device is used.

With reference to FIGS. 12-12B, the distal end 290 of the syringe barrel 282 may be constructed to cooperate as part of a connector interface. It may be generally cylindrical with a proximal Luer lock construction that may be made to comply with ISO standards 594-1 and 594-2. Described differently, it may be constructed to include a first cylindrical female portion 291 disposed coaxially around a first cylindrical male engaging portion 292, and a first engaging end defined by corresponding (although not necessarily coplanar) termini of the first cylindrical male portion 292 and the first cylindrical female portion 291, where the engaging end is the distal barrel end.

The Luer lock portion of the proximal end of the hub 266 may be constructed to comply with ISO standards 594-1 and 594-2. Stated differently, it may include a second cylindrical female portion 266*a* (of the hub) that engagingly receives therein the first male portion 292 of the syringe. The second cylindrical female portion 266*a* is constructed as a lumen defined by a second cylindrical male portion 266*b* that engages into the first female portion 291. A second engaging end (that is, the engaging end of the hub 266) is defined by the co-terminus of the second cylindrical male portion and the second cylindrical female portion.

The first cylindrical female portion 291 includes a helically-threaded surface that engagingly receives/interfaces with the externally-protruding tabs 266*c* of the second male portion 266*b* (which tabs may be embodied as at least one tab, one or more lugs, or threads). Complete rotational engagement of the tabs 266*c* with the threaded surface of the first female portion 291 corresponds with full engagement of the first male portion with the second female portion to form a fluid-patent connection. This may be enhanced when the first male engaging portion includes a tapered configuration including a smaller outer diameter near the engaging end and a larger outer diameter longitudinally spaced from the engaging end, and where the larger outer diameter engages an inner diameter of the second female portion to form at least part of the effective fluid-patent seal between the first and second connector elements.

A locking functionality of the connector interface may be provided by a tooth-notch engagement between the injector hub of the introducer assembly and the distal barrel end of the syringe. Those of skill in the art will appreciate that the connector interface described here may be used in a variety of other settings, including non-medical devices and assemblies. Fluid-patent connections using a Luer-lock-type construction and the presently-disclosed connection interface may readily be applied in the aerospace, automotive, and other industries. In particular, those of skill in the art will appreciate the usefulness and applicability of a fluid-patent connection interface that provides secure engagement and that also essentially provides for one-time use (where one or both elements of the connector interface will be damaged by disengagement after a complete engagement, thereby limiting re-use). Such single-use functionality will have readily-appreciated applicability in hygienic settings, as well as in other environments where there may be reasons for avoiding re-use such as potential food/liquid transport contamination, a need to provide visible indicia that a connection has been disengaged/tampered with, or other uses that will be appreciated by those having skill in the mechanical and related arts.

The hub 266 includes a plurality of teeth 269 extending generally longitudinally proximally along the outer surface of the second male portion 266*b*, proximal of the stop bar 268. The distal end of the syringe barrel 282 includes a corresponding plurality of notches 281. FIG. 12B shows the plunger 280 and a magnified (relative to the plunger) detail view of the barrel 282 (with the proximal portion shown as a longitudinal section). As shown in FIG. 12B, each notch 281 preferably is generally contoured as a right triangle with a first face 281*a* oriented at an acute angle relative to a plane defined by the barrel terminus and a second face 281*b* substantially perpendicular to the that plane.

Those of skill in the art will understand that, when the Luer lock male and female components are fully rotationally engaged, the teeth 269 will engage the notches 281. As the syringe barrel 282 is rotatingly engaged to the hub 266 by engagement of the tabs 266*c* into the threaded hub surface 291, the teeth 269 will press against the barrel's terminal surface plane until clicking past the second notch face 281*b* into the notch 281 and—as the threaded connection is further engaged—the teeth 269 will ride up the second notch face 281*b* in a manner biasing the hub away from the barrel and forcing the tabs/threads into tighter engagement.

Figure 13A:
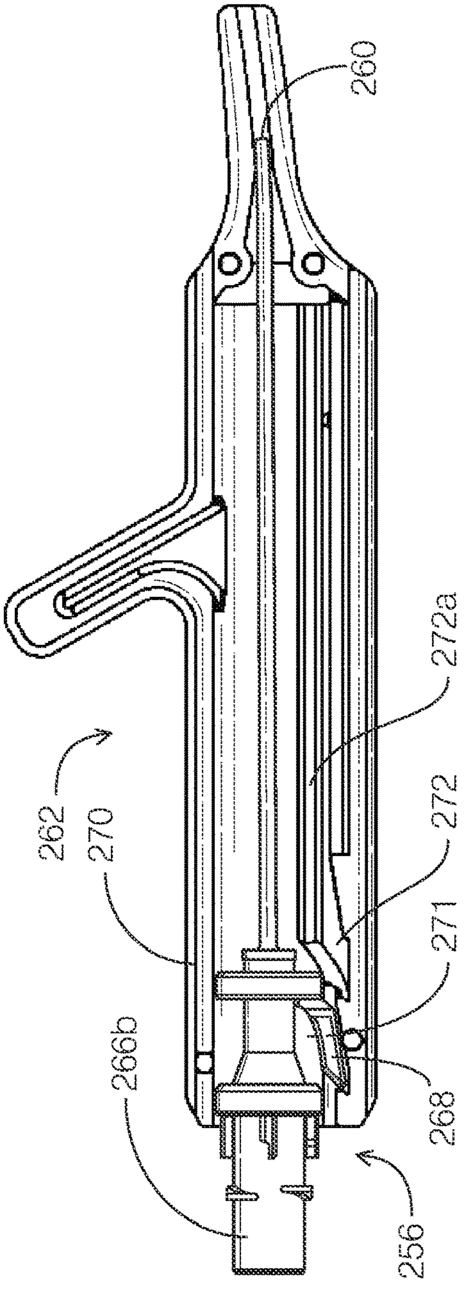
FIG. 13A shows an injector engaged into an introducer in a storage position.
Figure 13B:
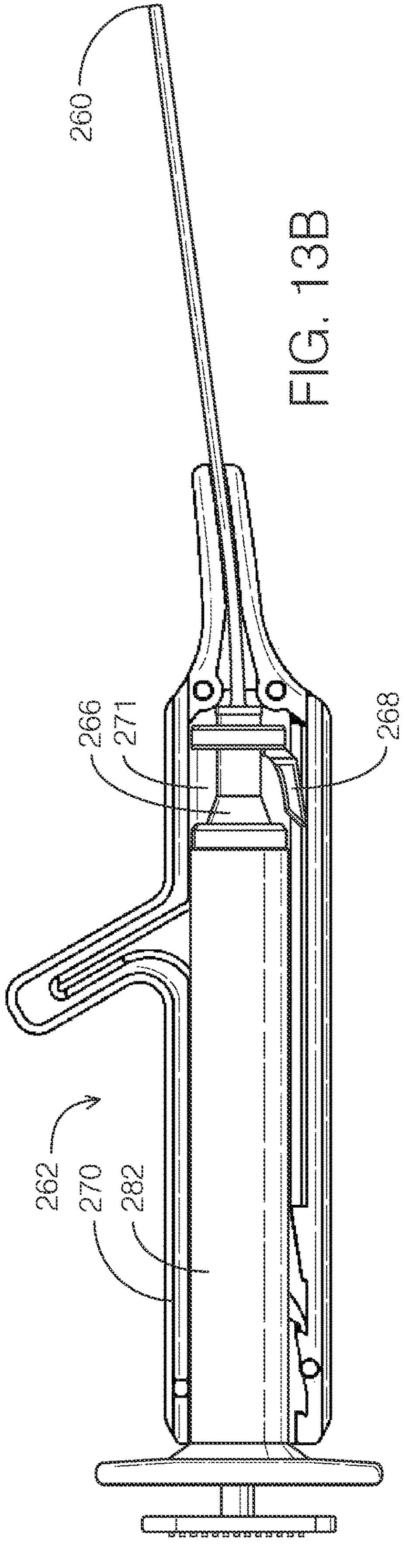
FIG. 13B shows a syringe attached to an injector that is in an engaged position within and relative to an introducer such that the barrel of the syringe is substantially received within the introducer and the injector will be aligned for SPG-targeted delivery (when used as directed transnasally).

The components all preferably are dimensioned so that complete engagement therebetween occurs at this point or form a locked relationship (engaged in a manner that requires damage to the longitudinal teeth and/or notches in order to reverse-rotate and disengage them from each other). In one preferred embodiment, the barrel and/or the teeth include a polymer construction (e.g., a polycarbonate) such that counter-rotation to disengage the pieces will bring the tooth up against the second notch face 281*a* and stop its progress unless over-forced sufficiently to damage the teeth and/or notch. In other embodiments, one or more components may include metal construction that would require even greater force to overcome the locking engagement. FIG. 13A shows an injector embodiment 266 of FIGS. 11-11B engaged into an introducer 262. FIG. 13B shows the injector 266 in an engaged/actuated state where its distal-most end extends out of the introducer to a position configured for medicament delivery to the SPG, and where the barrel of a syringe 282 engaged to an injector hub is received almost entirely within the body of the introducer 262 and the syringe plunger is shown as fully depressed (e.g., as if the syringe has been evacuated to deliver its entire contents).

It should be appreciated that the presently described embodiments are not limiting upon the uses of the locking mechanism described here. Specifically, by way of example, the tooth/notch locking mechanism described here may be implemented in other (e.g., non-medical) devices. For example, fluid-flow couplings in industrial equipment may be constructed with traditional luer-lock components and the novel outer locking structure presented herein. Those of skill in the mechanical arts will appreciate from the present disclosure (including the drawings) that the inventive tooth/notch locking system allows a user to rotatingly "lock closed/engaged" the luer-lock components. Depending upon the materials used, counter-rotation to unlock those components preferably will either not be possible, or will be sufficiently destructive to the components so as to render the connector assembly effectively a single-use locking mechanism. For example, providing generally rigid stainless steel for both the teeth and the notches will allow a single-use (e.g., substantially permanent) locking, or one-time locking, structure, while using a deformable or breakable polymer will do the same. For example, once locked, the mechanism cannot be unlocked without modifying or breaking it. The phrase "Luer-lock" and components or elements thereof will readily be understood by those of skill in the mechanical arts with reference to the state of the art, to ISO 594 standards, although the present claims are not limited to a 6° taper for inner connections, as those of skill in the art will readily adapt the fitting components in special applications to other angles when needed.

Those having skills in the mechanical arts will appreciate from the present disclosure the novelty and usefulness of a luer-lock-type connector, applicable in a variety of medical, industrial, and other settings where a fluid-patent or otherwise secure, one-time lockable connection is desirable. Accordingly, in one aspect, embodiments presently disclosed may include a luer-lock connector interface that includes a first Luer lock element with a cylindrical end including a plurality of asymmetrical notches where each of the notches includes a first face at an acute angle relative to a plane defined by the cylinder end and a second face at substantially a perpendicular angle relative to said plane; a second luer-lock element including a plurality of teeth that engage the notches and prevent disengaging counter-rotation of the second luer-lock element from the first luer-lock element after a complete engagement therebetween.

All manner of medicaments suitable for introduction at or in the vicinity of the SPG are contemplated for use in accordance with the present teachings. The physical state of the medicament includes but is not limited to liquids, solids, semi-solids, suspensions, powders, pastes, gels, and the like, and combinations thereof. In some embodiments, the medicament is provided in an at least partially liquid form. In preferred embodiments of the present disclosure, the medicament contains CBD in an aqueous solution or suspension, which may be a saline aqueous solution or suspension, and where CBD should be understood to include effective derivatives and/or variants of Formula I referenced above, or one or more of Dimethyltryptamine (DMT), Psilocybin, Δ8-tetrahydrocannabinol, and Δ9-tetrahydrocannabinol.

In some embodiments, the medicament used in accordance with the present teachings is provided in a container 14 (shown in FIGS. 1, 3, 4) as a pressured or aerosolized mixture, or may be loaded into a syringe such as the syringe embodiment shown in FIGS. 12-12B, or another syringe, the barrel of which will be received into the lumen 271 of the housing 270 when the injector 256 is advanced distally (e.g., as shown in the transition from FIGS. 6 and 7 to FIG. 8). The medicament optionally contains preservatives, a liquid carrier, and/or other inert ingredients and additives as will be readily appreciated by those of ordinary skill in the art.

The amount of medicament delivered in accordance with the present teachings can be readily determined by one of ordinary skill in the art and will vary according to factors such as the nature and/or concentration of the medicament, the patient's age, condition, and/or sensitivity to the medicament, and the like. In some embodiments, the dosage volume ranges from about 0.1 cc to about 1.0 cc, containing a therapeutically effective amount of CBD or other identified medicament. In some embodiments, the dosage volume is about 0.5 cc containing a therapeutically effective amount of CBD or other identified medicament at a concentration in the ranges identified above. (NOTE: throughout the present application, unless the context is specifically limited to CBD, the method described should be understood to include one or more of CBD, Dimethyltryptamine (DMT), Psilocybin, Δ8-tetrahydrocannabinol, and Δ9-tetrahydrocannabinol).

Methods and devices described herein are contemplated for use in the treatment of all manner of conditions for which the introduction of a medicament superiorly and/or laterally and/or anteriorly towards the SPG of a patient is desirable. For example, the present methods may also be effective for preventing or at least reducing the incidence and/or severity of certain types of seizures, and all other conditions for which one or more of CBD, Dimethyltryptamine (DMT), Psilocybin, Δ8-tetrahydrocannabinol, and Δ9-tetrahydrocannabinol, is known to be effective, including on-label and off-label uses and particularly with reference to conditions for which published and unpublished clinical and anecdotal data exist that shows efficacy of CBD and/or the other identified medicaments for treating particular conditions and/or disorders whether or not specifically identified herein.

Topical administrations of a medicament to human tissue for the systemic delivery of a pharmaceutically active agent typically include the use of transdermal and/or transmucosal pastes, creams, liquids, solids, semisolids, and the like. However, systemic delivery of pharmaceutically active agents by topical administration is hampered by the difficulty of diffusing an agent through the tissue to which the agent is applied in order to reach blood vessels, whereby the agent can then be absorbed for systemic delivery, and the same or similar challenges may apply where the medicament is absorbed internally via peroral dosage/ingestion. Thus, to address this difficulty, the methods and devices described herein may be invoked to achieve increased permeability of the blood brain barrier in the administration of any medicament. In view of the surprisingly effective clinical results described below, the transnasal delivery of a therapeutically effective dose that is well below the standard peroral doses is expected to reduce the likelihood and incidence of side effects, particularly those associated with higher dosages and/or with by-products from gastro-intestinal metabolism (including in the liver) of peroral administration.

The term "kit" refers to an assembly of materials that are used in performing a method in accordance with the present teachings. Such kits can include one or a plurality of devices and/or components thereof, including but not limited to the representative devices described above, and may further include one or more medicaments to be used therewith.]

In some embodiments, a kit includes an injector and/or an introducer, each of which is configured for engagement with a left-side nostril of the patient. In some embodiments, a kit includes an injector and/or an introducer configured for engagement with a right-side nostril of the patient. In some embodiments, a kit includes an injector and an introducer configured for engagement with a left-side nostril of the patient, as well as an injector and an introducer configured for engagement with a right-side nostril of the patient. Optionally, an interchangeable handle can also be provided for connection to either of the right-handed and left-handed introducers. In other embodiments, the handle itself exhibits handedness, and separate handles can be provided for each of the right-handed introducer and the left-handed introducer, where—in any event—the medicament may be delivered via one or both nostrils (e.g., one-half each, or some other fractional division resulting in a whole dose).

In some embodiments, the device will be provided in a fully assembled state, while in other embodiments assembly of the device will be required. In some embodiments, the device provided in the kit includes a delivery tube having a curved portion at one of its ends configured for insertion into a patient's nostril, wherein the delivery tube is housed within a substantially cylindrical (e.g., pen- or cigar-shaped) housing, such as the type described above. In some embodiments, one or a plurality of the components of the device is disposable and, optionally, biodegradable.

The medicament may be provided in a kit as a single reagent or a plurality of reagents. Representative medicaments for use in accordance with the present teachings include but are not limited to those described above. The medicaments may be provided in packaged combination in the same or in separate containers, depending on their cross-reactivities and stabilities, and in liquid or in lyophilized form. The amounts and proportions of any reagents provided in the kit may be selected so as to provide optimum results for a particular application. In other embodiments, the device may be provided in the kit, and the medicament may be obtained separately. For example, a peroral tablet may be obtained, crushed, and dissolved/suspended into water or another delivery liquid that preferably is sterile and/or otherwise appropriate for pharmaceutical use in delivering medicament transnasally. The water may include or may have added other components to provide pH buffering, salinity, or other desired qualities.

Kits in accordance with the present teachings may also be supplied with other items known in the art and/or which may be desirable from a commercial and user standpoint, such as empty syringes, tubing, gauze, pads, disinfectant solution, cleaning solutions, instructions for performing a transnasal delivery of medicament, and/or for assembling, using, and/or cleaning the device, and the like, and combinations thereof.

In some embodiments, instructions may be affixed to one or more components of the device and/or the containers (e.g., vials), or to a larger container in which one or more components of the kit are packaged for shipping. The instructions may also be provided as a separate insert, termed the package insert. Instructional materials provided with kits may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail.

In use, the optional handle 20 of the devices 10 described herein can be pushed towards the patient's face until introducer 18 snugly and comfortably engages and fits within the patient's nostril to lift the flat tip of the patient's nose to point superiorly and slightly posteriorly. Thereafter, the injector 12 can be pushed posteriorly towards the patient's nose to slide tubular section 24 and nozzle 28 rearwardly until nozzle 28 is located medially and/or posteriorly and/or inferiorly to the SPG—medially and/or inferiorly in some embodiments, and medially, inferiorly, and posteriorly in other embodiments. Thereafter, a medicament such as a mixture, solution, emulsion, or suspension including one or more of CBD, Dimethyltryptamine (DMT), Psilocybin, Δ8-tetrahydrocannabinol, and Δ9-tetrahydrocannabinol (and/or any effective variant or derivative thereof) can be injected and sprayed through apertures 36 of nozzle 28 upwardly and/or laterally and/or anteriorly towards and about the SPG to treat a patient—where the spray is directed toward the SPG laterally and/or upwardly in some embodiments, and laterally, upwardly, and anteriorly in other embodiments.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

I claim:

1. A method for treating a disorder in a human patient, comprising steps of:

transnasally administering to the patient a therapeutically effective amount of a medicament comprising one or more of CBD, Dimethyltryptamine (DMT), Psilocybin, Δ8-tetrahydrocannabinol, and Δ9-tetrahydrocannabinol, or any effective variant or derivative thereof;

wherein the transnasal administration step includes spraying the medicament from within the patient's nasal cavity, directed laterally and superiorly toward the sphenopalatine ganglion of the patient.

2. The method of claim 1, wherein the medicament is dissolved or suspended in water, providing a liquid volume deliverable, at a concentration of about 1 mg/mL to about 40 mg/mL.

3. The method of claim 2, wherein the volume of liquid delivered is about 0.1 mL to about 1 mL.

4. The method of claim 2, wherein the volume of liquid delivered does not exceed 1 mL and the amount of the medicament is about 1 mg to about 40 mg.

5. The method of claim 1, wherein the step of transnasally administering is performed between once per week and once per two months, and where the therapeutically effective amount of the medicament is between 1 mg and 40 mg.

6. The method of claim 1, wherein the transnasal administration step includes using a delivery device that comprises:

an injector including a first end configured to remain outside a nasal passage of the patient and a second end configured for entry into the nasal passage of the patient, where the second end is configured for fluid communication with a syringe; and an introducer configured for engagement partially into a nostril of the patient;

where a distal portion of the injector includes a lateral-side aperture through which the medicament is sprayed.

7. A kit for effecting the method of claim 6, said kit comprising a syringe, the introducer, and the injector.

8. The method of claim 6, further comprising steps of:

introducing the medicament into the syringe;

attaching the syringe to the injector;

engaging a distal portion of the introducer partially into a nostril of the patient;

directing the syringe into the introducer in a manner that distally advances the injector through the distal portion of the introducer into a nostril of the patient so that the aperture is adjacent inferiorly, laterally, and/or posteriorly relative to the sphenopalatine ganglion; and actuating the syringe to effect the transnasal administration step by spraying the medicament through the aperture.

9. The method of claim 1, wherein a selected one or more of CBD, Dimethyltryptamine (DMT), Psilocybin, Δ8-tetrahydrocannabinol, and Δ9-tetrahydrocannabinol, or any effective variant or derivative thereof, is delivered without co-delivery of another material.

10. The method of claim 1, wherein the medicament is obtained from a tablet or emptied from a capsule, then dissolved or suspended in water or another carrier liquid, providing a liquid deliverable, at a concentration of about 1 mg/mL to about 40 mg/mL.

11. The method of claim 1, where the therapeutically effective amount is a therapeutically effective amount for alleviating one or more symptoms of a disorder selected from one or more of self-reported or clinically-diagnosed depression, substandard sleep quality, appetite control issues, social anxiety, general anxiety, PTSD, traumatic memory-related stress, cluster headaches, intractable phantom-limb pain (PLP), chronic pain, and/or obsessive-compulsive disorders (OCD).

12. The method of claim 1, where the therapeutically effective amount is a therapeutically effective amount for treating appetite control, where the therapeutic amount is at a concentration of about 1 mg/mL to about 40 mg/mL, delivered in an aqueous solution or suspension.

13. The method of claim 12, where the aqueous solution or suspension comprises a volume of about 0.1 mL to about 5 mL.

14. The method of claim 1, where a first portion of the medicament is delivered via a patient's right nostril and a second portion of the medicament is delivered via a patient's left nostril.

15. A method for treating a disorder in a human patient, comprising steps of:

transnasally administering to the patient a therapeutically effective amount of a medicament comprising one or more of CBD, Dimethyltryptamine (DMT), Psilocybin, Δ8-tetrahydrocannabinol, and Δ9-tetrahydrocannabinol, or any effective variant or derivative thereof;

wherein the transnasal administration step includes spraying the medicament from within the patient's nasal cavity, directed laterally and superiorly toward the sphenopalatine ganglion of the patient, wherein the transnasal administration step includes using a delivery device that comprises:

an injector including a first end configured to remain outside a nasal passage of the patient and a second end configured for entry into the nasal passage of the patient, where the second end is configured for fluid communication with a syringe; and an introducer configured for engagement partially into a nostril of the patient;

where a distal portion of the injector includes a lateral-side aperture through which the medicament is sprayed;

wherein the introducer comprises a passageway that slidably receives the injector, and the passageway slidably receives within the introducer a barrel portion of the syringe when the syringe is attached to the injector and the injector is advanced distally out of the passageway, and wherein the injector lateral-side aperture is disposed at an acute angle relative to a central longitudinal axis of the introducer; and wherein the injector is moveable, relative to the introducer, between a storage position at least partially within the introducer and an engaging position where the injector extends from the introducer sufficiently to position the aperture within the patient's nasal cavity inferiorly, laterally, and/or posteriorly relative to the patient's sphenopalatine ganglion.

16. A method for treating a human patient, comprising steps of:

administering a therapeutically effective amount, for alleviating symptoms of self-reported or clinically-diagnosed depression, substandard sleep quality, appetite control issues, social anxiety, general anxiety, PTSD, traumatic memory-related stress, cluster headaches, intractable phantom-limb pain (PLP), chronic pain, and/or obsessive-compulsive disorders (OCD), of a medicament comprising one or more of CBD, Dimethyltryptamine (DMT), Psilocybin, Δ8-tetrahydrocannabinol, and Δ9-tetrahydrocannabinol, or any effective variant or derivative thereof by transnasally administering the medicament to the sphenopalatine ganglion of a patient, directed laterally and superiorly toward the sphenopalatine ganglion of the patient, wherein the therapeutically effective amount is lower than a therapeutically effective amount required for the same therapeutic effect via oral or standard nasal spray administration of the same medicament.

17. The method of claim 16, wherein delivery is effected via a tube inserted into the patient's nasal cavity;

wherein the transnasal administration step includes spraying the medicament from within the patient's nasal cavity laterally and superiorly toward the sphenopalatine ganglion.

18. The method of claim 16, where the transnasal administration step includes anteriorly directed spraying.

19. A method for treating a human patient, comprising steps of:

providing a means for delivering a medicament to the sphenopalatine ganglion of a patient;

administering a therapeutically effective amount of a medicament for alleviating symptoms of one or more of self-reported or clinically-diagnosed depression, substandard sleep quality, appetite control issues, social anxiety, general anxiety, PTSD, traumatic memory-related stress, cluster headaches, intractable phantom-limb pain (PLP), chronic pain, and/or obsessive-compulsive disorders (OCD);

wherein the medicament comprises one or more of CBD, Dimethyltryptamine (DMT), Psilocybin, Δ8-tetrahydrocannabinol, and Δ9-tetrahydrocannabinol, or any effective variant or derivative thereof; and wherein the step of administering comprises transnasally delivering the medicament to the sphenopalatine ganglion of the patient by directing a distal portion of the means for delivering the medicament transnasally to a location inferior and lateral of the sphenopalatine ganglion and actuating the means for delivering the medicament in a manner that directs the medicament toward the sphenopalatine ganglion.

* * * * *